United States Patent
Miyashita et al.

(10) Patent No.: US 11,557,727 B2
(45) Date of Patent: Jan. 17, 2023

(54) ORGANIC PHOTOELECTRIC CONVERSION ELEMENT, IMAGE PICKUP ELEMENT, AND IMAGE PICKUP APPARATUS

(71) Applicant: CANON KABUSHIKI KAISHA, Tokyo (JP)

(72) Inventors: Hirokazu Miyashita, Ebina (JP); Naoki Yamada, Inagi (JP); Hiroki Ohrui, Kawasaki (JP); Hironobu Iwawaki, Yokohama (JP); Yosuke Nishide, Kawasaki (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 155 days.

(21) Appl. No.: 16/714,290

(22) Filed: Dec. 13, 2019

(65) Prior Publication Data

US 2020/0119281 A1    Apr. 16, 2020

Related U.S. Application Data

(63) Continuation of application No. PCT/JP2018/023152, filed on Jun. 18, 2018.

(30) Foreign Application Priority Data

Jun. 23, 2017 (JP) ............................. JP2017-123089

(51) Int. Cl.

| H01L 51/00 | (2006.01) |
|---|---|
| H01L 27/30 | (2006.01) |
| H01L 51/42 | (2006.01) |
| H04N 5/378 | (2011.01) |
| C07D 209/86 | (2006.01) |
| C07D 409/14 | (2006.01) |
| C07D 401/14 | (2006.01) |
| H01L 51/44 | (2006.01) |

(52) U.S. Cl.
CPC ........ *H01L 51/0046* (2013.01); *H01L 27/307* (2013.01); *H01L 51/4273* (2013.01); *H04N 5/378* (2013.01); *H01L 51/441* (2013.01)

(58) Field of Classification Search
None
See application file for complete search history.

(56) References Cited

U.S. PATENT DOCUMENTS

2018/0026202 A1 * 1/2018 Danz .................... C07D 219/08
257/40

FOREIGN PATENT DOCUMENTS

| CN | 106146317 A | 11/2016 |
|---|---|---|
| JP | 2011-187937 A | 9/2011 |
| JP | 2013-155153 A | 8/2013 |
| JP | 2017-5249 A | 1/2017 |
| KR | 10-2015-0086994 A | 7/2015 |
| WO | 2014/167860 A1 | 10/2014 |
| WO | 2016/021266 A1 | 2/2016 |
| WO | 2017/005699 A1 | 1/2017 |

* cited by examiner

*Primary Examiner* — Po-Chih Chen
(74) *Attorney, Agent, or Firm* — Canon U.S.A., Inc., IP Division

(57) ABSTRACT

The present disclosure provides an organic compound represented by general formula [1] below.

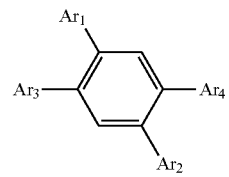

[1]

In formula [1], $Ar_1$ and $Ar_2$ each represent an alkyl group having 1 to 8 carbon atoms, an aromatic hydrocarbon group having 6 to 18 carbon atoms, or a heteroaromatic group having 3 to 17 carbon atoms. $Ar_1$ and $Ar_2$ may be the same or different. $Ar_3$ and $Ar_4$ are each a substituent having a carbazolyl group. $Ar_3$ and $Ar_4$ may be the same or different. $Ar_1$ to $Ar_4$ may be substituted. At least one of $Ar_1$ to $Ar_4$ has a tert-butyl group. The total number of tert-butyl groups in one molecule of the organic compound is 2 or more.

5 Claims, 5 Drawing Sheets

ORGANIC PHOTOELECTRIC CONVERSION ELEMENT, IMAGE PICKUP ELEMENT, AND IMAGE PICKUP APPARATUS

CROSS-REFERENCE TO RELATED APPLICATIONS

This application is a Continuation of International Patent Application No. PCT/JP2018/023152, filed Jun. 18, 2018, which claims the benefit of Japanese Patent Application No. 2017-123089, filed Jun. 23, 2017, both of which are hereby incorporated by reference herein in their entirety.

TECHNICAL FIELD

The present invention relates to an organic photoelectric conversion element, an image pickup element including the organic photoelectric conversion element, and an image pickup apparatus including the organic photoelectric conversion element.

BACKGROUND ART

Planar light-receiving elements are widely used as image pickup elements in cameras and the like. Such a planar light-receiving element includes a two-dimensional array of pixels having photodiodes. Upon receiving light, the planar light-receiving element generates a signal. The signal is read out, and a CCD circuit or a CMOS circuit performs image processing. In the related art, silicon and other semiconductor substrates having photoelectric conversion units formed therein are used as the above image pickup elements.

Elements including photoelectric conversion units made of organic compounds, that is, organic photoelectric conversion elements are under development. It is expected that high absorption coefficients and flexibility of organic compounds enable image pickup elements having improved properties such as higher sensitivity, slimmer profiles, lighter weights, and higher flexibility.

In such image pickup elements, dark current is known to cause degradation of the quality of captured images. Various studies have been conducted to reduce dark current in organic photoelectric conversion elements.

PTL 1 discloses that after an element is fabricated, heat treatment (annealing) at high temperature is performed to reduce dark current.

PTL 2 discloses that a compound represented by the following structural formula (hereinafter referred to, for example, as compound 1-A) is used in an organic light-emitting element.

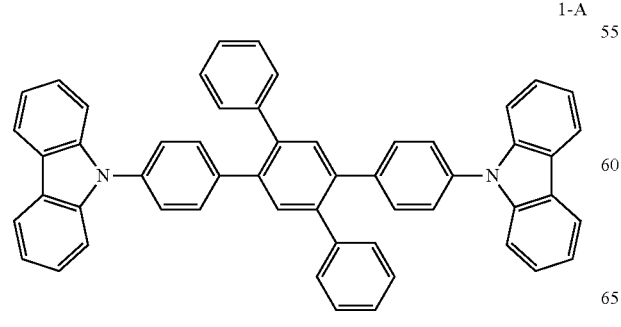

1-A

To reduce dark current, it is preferable to perform sublimation purification of an organic compound used in an organic photoelectric conversion element or to perform an annealing step after the organic photoelectric conversion element is fabricated. However, high-temperature annealing of an organic compound layer may cause the organic compound to undergo crystallization, which can lead to degradation of element properties. As well as preferred examples, PTL 1 also discloses that after annealing, dark current is increased rather than decreased to reduce external quantum efficiency.

Compound 1-A disclosed in PTL 2 does not have a sufficiently high glass transition temperature, and thus may undergo crystallization in a high-temperature annealing step, leading to degradation of element properties.

The present invention has been made to overcome the above disadvantages, and an object thereof is to provide an organic compound having high sublimability and a high glass transition temperature.

CITATION LIST

Patent Literature

PTL 1: Japanese Patent Laid-Open No. 2011-187937
PTL 2: Korean Patent Laid-Open No. 2015-0086994

SUMMARY OF INVENTION

Thus, the present invention provides an organic compound represented by general formula [1] below.

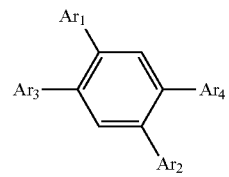

[1]

In formula [1], $Ar_1$ and $Ar_2$ represent an alkyl group having 1 to 8 carbon atoms, an aromatic hydrocarbon group having 6 to 18 carbon atoms, or a heteroaromatic group having 3 to 17 carbon atoms. $Ar_1$ and $Ar_2$ may be the same or different. $Ar_3$ and $Ar_4$ are selected from the group consisting of substituents represented by general formulae [2a] to [2c]. $Ar_3$ and $Ar_4$ may be the same or different.

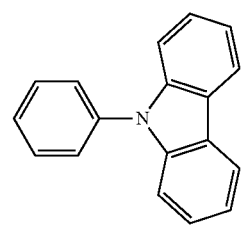

[2a]

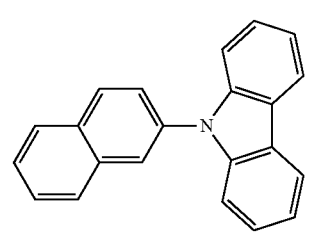

[2b]

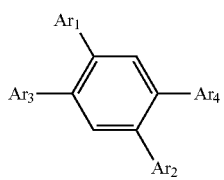

[2c]

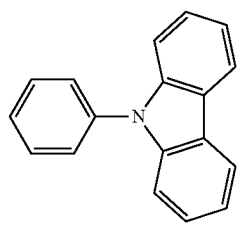

[2a]

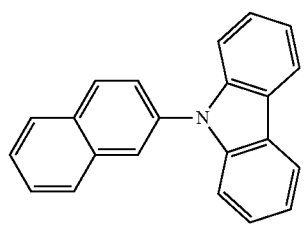

[2b]

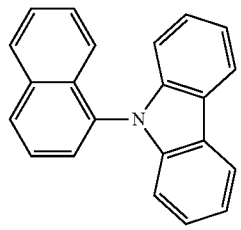

[2c]

$Ar_1$ to $Ar_4$ are each optionally substituted with a substituent selected from the group consisting of a halogen atom, a cyano group, an alkyl group having 1 to 8 carbon atoms, and an alkoxy group having 1 to 8 carbon atoms. The alkyl group is optionally substituted with a fluorine atom. At least one of $Ar_1$ to $Ar_4$ has a tert-butyl group. The total number of tert-butyl groups in one molecule of the organic compound is 2 or more.

Further features of the present invention will become apparent from the following description of exemplary embodiments with reference to the attached drawings.

DESCRIPTION OF EMBODIMENTS

Figure 1:
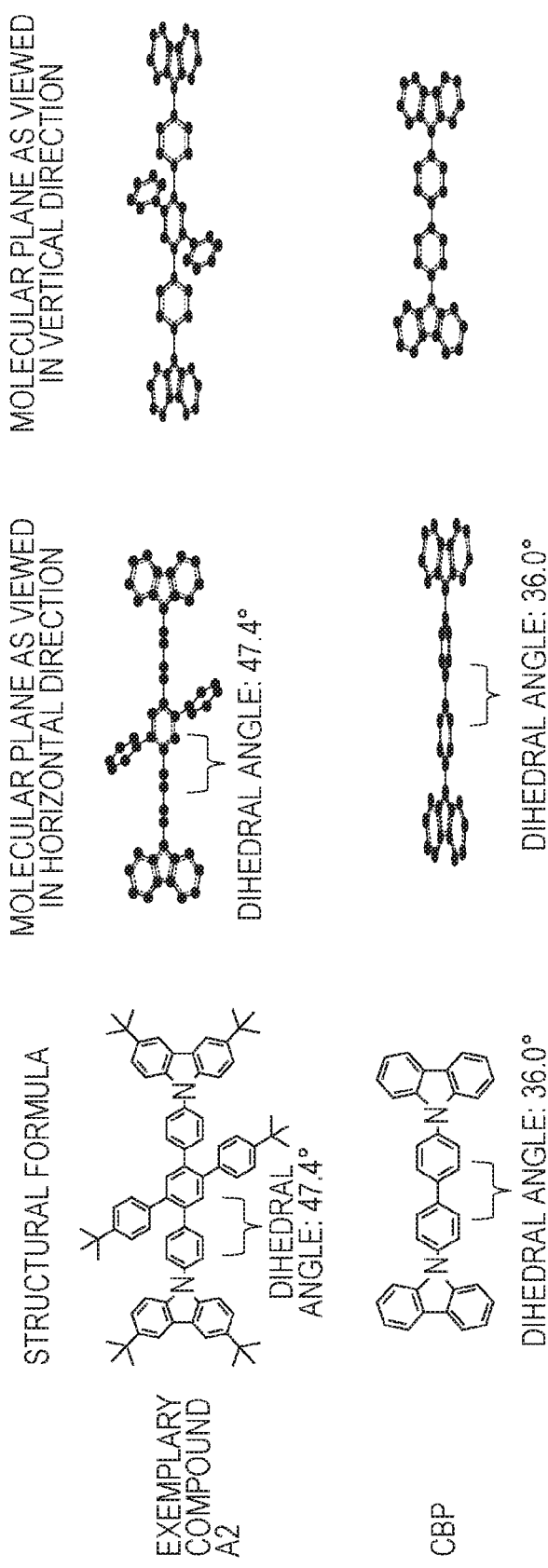
FIG. 1 schematically illustrates a molecular structure of exemplary compound A2 and a molecular structure of comparative compound 1.

The present invention is an organic compound represented by general formula [1] below.

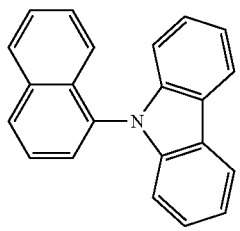

[1]

In formula [1], $Ar_1$ and $Ar_2$ each represent an aromatic hydrocarbon group having 6 to 18 carbon atoms or a heteroaromatic group having 3 to 17 carbon atoms. $Ar_3$ and $Ar_4$ are selected from the group consisting of substituents represented by general formulae [2a] to [2c] below. At least one of $Ar_1$ to $Ar_4$ has a tert-butyl group.

Examples of aromatic hydrocarbon groups represented by $Ar_1$ and $Ar_2$ include phenyl, naphthyl, phenanthryl, fluorenyl, chrysenyl, triphenylenyl, and pyrenyl. From the viewpoint of sublimability, substituents having relatively small molecular weights are preferred. Specifically, phenyl and naphthyl are preferred.

Examples of heteroaromatic groups represented by $Ar_1$ and $Ar_2$ include pyridyl, pyrazinyl, pyrimidinyl, quinolyl, isoquinolyl, thienyl, furanyl, benzothienyl, benzofuranyl, and triazinyl. From the viewpoint of sublimability and stability, substituents having relatively small molecular weights and high stability are preferred. Specifically, pyridyl, benzothienyl, and benzofuranyl are preferred.

$Ar_3$ and $Ar_4$ are substituents selected from the group consisting of substituents represented by general formulae [2a] to [2c]. Of the substituents represented by formulae [2a] to [2c], the substituent represented by formula [2a], which has a relatively small molecular weight, is preferred in view of sublimability.

$Ar_1$ to $Ar_4$ may be substituted with a halogen atom, for example, fluorine, chlorine, bromine, or iodine, preferably, fluorine.

$Ar_1$ to $Ar_4$ may be substituted with a cyano group.

$Ar_1$ to $Ar_4$ may be substituted with an alkyl group, for example, an alkyl group having 1 to 8 carbon atoms. Specific examples include methyl, ethyl, n-propyl, iso-propyl, n-butyl, iso-butyl, sec-butyl, tert-butyl, n-pentyl, n-hexyl, cyclohexyl, n-heptyl, and n-octyl. Methyl and tert-butyl are preferred. The alkyl group may be substituted with a fluorine atom. The alkyl group substituted with a fluorine atom is preferably a trifluoromethyl group.

$Ar_1$ to $Ar_4$ may be substituted with an alkoxy group, for example, an alkoxy group having 1 to 8 carbon atoms. Specific examples include methoxy, ethoxy, propoxy, butoxy, pentoxy, and hexoxy. Methoxy is preferred.

At least one of $Ar_1$ to $Ar_4$ has a tert-butyl group, and the total number of tert-butyl groups contained in $Ar_1$ to $Ar_4$ is 2 or more. Preferably, the total number of tert-butyl groups contained in $Ar_1$ to $Ar_4$ is 4 or more.

The total number of tert-butyl groups contained in $Ar_1$ to $Ar_4$ is 2 or more. This is because the electron blocking ability and thermal stability of the organic compound cannot sufficiently be improved when the number of tert-butyl groups is 1.

The total number of tert-butyl groups contained in $Ar_1$ to $Ar_4$ is preferably 4 or more, more preferably 6 or more. In view of hole transportability, the number of tert-butyl groups is preferably 10 or less. That is, the number of tert-butyl groups in one molecule of the organic compound according to the present invention may be 2 to 10, 4 to 10, or 6 to 10.

The organic compound according to the present invention has a high glass transition temperature and a low LUMO level and thus can be used, for example, for an electron blocking layer of an organic electronic element. The electron blocking layer is a layer less likely to receive electrons. LUMO means the lowest unoccupied molecular orbital. Having a low LUMO level means having a LUMO level closer to the vacuum level. A low LUMO level is also expressed as a shallow LUMO level. The same can be said for a HOMO (highest occupied molecular orbital) level.

Characteristics of Organic Compound According to Present Invention

The organic compound according to the present invention has a benzene ring substituted with $Ar_1$ to $Ar_4$, as represented by general formula [1]. $Ar_3$ and $Ar_4$ each have a carbazolyl group, as shown in general formulae [2a] to [2c]. At least one of $Ar_1$ to $Ar_4$ has a tert-butyl group, and the total number of tert-butyl groups contained in $Ar_1$ to $Ar_4$ is 2 or more. With this configuration, the compound of general formula [1] has the following characteristics (1) to (6).
(1) Being readily formed into an amorphous thin film
(2) Having a wide band gap and low absorption in the visible light range
(3) Having high hole transportability
(4) Having high electron blocking ability
(5) Having high thermal stability
(6) Having high sublimability These characteristics will be described below.

(1) Being Readily Formed into an Amorphous Thin Film

The organic compound according to the present invention has a benzene ring substituted with $Ar_1$ to $Ar_4$, as represented by general formula [1]. With this configuration, repulsion due to steric hindrance occurs to cause the whole molecule to have a twisted structure. Here, the molecular structure of exemplary compound A2 according to the present invention and comparative compound 1 in FIG. 1, which is a compound having a structure represented by general formula [1] where $Ar_1$ and $Ar_2$ are each a hydrogen atom and $Ar_3$ and $Ar_4$ are each represented by formula [2a], was estimated by molecular orbital calculation. The planarity of the estimated molecular skeletons was evaluated by comparing their dihedral angles. The dihedral angles compared were dihedral angles between the benzene ring in general formula [1] and its adjacent benzene ring. FIG. 1 illustrates molecular structures of exemplary compound A2 and comparative compound 1 as observed in the horizontal direction and the vertical direction. The dihedral angle of comparative compound 1 was 36.0°, whereas the dihedral angle of exemplary compound A2 according to the present invention was 47.4°. Exemplary compound A2 was found to have a highly twisted structure.

An organic compound having such a twisted structure is less likely to undergo molecular packing. Molecular packing is a phenomenon where molecules are stacked on top of each other by intermolecular interaction. Aromatic compounds have highly planar molecular skeletons and strong intermolecular interactions and thus are likely to undergo accelerated molecular packing. Compounds having a carbazolyl group are also likely to undergo molecular packing because the carbazolyl group itself has high planarity. Molecular packing is unfavorable because it can cause crystallization.

Molecular packing can be reduced, for example, by incorporating many substituents, but this method involves an increase in molecular weight and thus is not preferred from the viewpoint of sublimability. The organic compound according to the present invention, whose basic molecular skeleton itself is twisted and which has a nonplanar molecular structure, is less likely to undergo molecular packing. Therefore, the organic compound according to the present invention is readily formed into an amorphous thin film.

To achieve high external quantum efficiency and low dark current in an organic photoelectric conversion element, it is preferable to use a compound formable into an amorphous film. This is because a film having a grain boundary traps carriers to cause a decrease in photoelectric conversion efficiency and an increase in dark current. The same can be said for an electron blocking layer and a hole blocking layer disposed between a photoelectric conversion layer and an electrode.

In particular, an organic compound layer in contact with an electrode is preferably an amorphous thin film. This is because a film in an aggregated state induced by crystallization is ununiform, and accordingly the electric field may be locally concentrated in the film. Such a local electric field concentration can cause a leakage current or an in-plane variation in sensitivity, thus reducing the stability of element properties.

Thus, the organic compound according to the present invention is readily formed into an amorphous thin film and hence is suitable for use as a constituent material of an organic photoelectric conversion element.

The molecular orbital calculation was performed by the density functional theory (DFT), which is now widely used. The B3LYP functional and the 6-31G* basis function were used. The molecular orbital calculation was performed by Gaussian 09 (Gaussian 09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V.

Ortiz, J. Cioslowski, and D. J. Fox, Gaussian, Inc., Wallingford Conn., 2010), which is now widely used.

(2) Having a Wide Band Gap and Low Absorption in the Visible Light Range

As described above, the organic compound according to the present invention has a benzene ring substituted with $Ar_1$ to $Ar_4$, as represented by general formula [1], and thus the whole molecule has a twisted structure. Due to this structure, the conjugation of molecules is broken, and thus the compound has a wide band gap. That is, the compound has a wide band gap and low absorption in the visible light range. The wide band gap is also due to the reduced molecular packing described in (1). It is known that an organic compound, when formed into a thin film, experiences a phenomenon in which the apparent conjugation length is increased by molecular packing and the absorption wavelength becomes longer, that is, the band gap becomes narrower. The compound of general formula [1] according to the present invention has a structure that can sufficiently reduce molecular packing and thus is less likely to have a narrower band gap when formed into a thin film.

In an organic photoelectric conversion element, a larger amount of light preferably reaches a photoelectric conversion layer. For example, in the case of a structure in which an electron blocking layer or the like is disposed on the light incident side of the photoelectric conversion layer, when the electron blocking layer has absorption in the visible range, the amount of light reaching the photoelectric conversion layer is small, leading to low external quantum efficiency. Therefore, the electron blocking layer is preferably formed of a compound having low absorption in the visible range.

On the other hand, the electron blocking layer preferably has a large thickness to sufficiently suppress electron injection from an electrode. If the thickness is not sufficiently large, tunnel electron injection may occur when a voltage is applied, or irregularities and foreign matter on the electrode surface cannot sufficiently be covered, which may cause a physical short circuit or a leakage current.

When the thickness is not sufficiently large, the layer is less likely to have a uniform thickness. In this case, the photoelectric conversion layer and the electrode are locally adjacent to each other, and thus the electric field may be concentrated in the adjacent area to cause charge injection from the electrode.

Therefore, the electron blocking layer is preferably formed of a compound that, when formed into a layer with a sufficiently large thickness, has low absorption in the visible light range so as not to reduce the amount of light reaching the photoelectric conversion layer.

Figure 2:
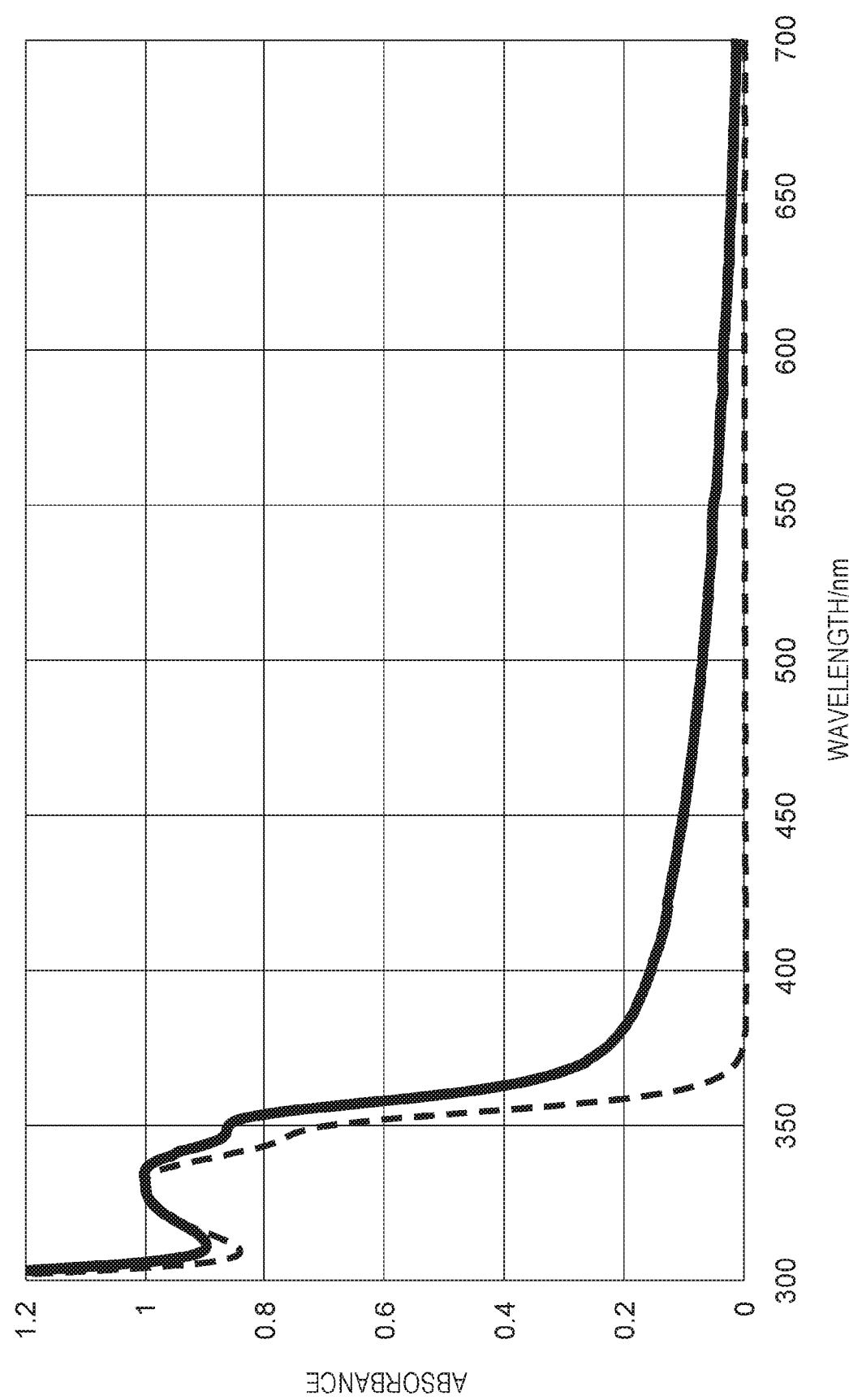
FIG. 2 is a graph of an absorption spectrum of exemplary compound A2 in a solution and an absorption spectrum of a thin film formed from the solution.

FIG. 2 is a graph of absorption spectra of a diluted toluene solution (dotted line) of exemplary compound A2 according to the present invention and its deposited film (solid line). The optical band gaps of exemplary compound A2 were calculated from absorption edges in the absorption spectra; the band gap estimated from the toluene solution was 3.42 eV, and the band gap estimated from the deposited film was 3.36 eV. The results show that the band gap slightly becomes narrower by 0.06 eV after the thin film formation.

The fact that the band gap after the thin film formation is 3.36 eV (369 nm, in terms of wavelength) indicates that exemplary compound A2 has sufficiently low absorption in the visible light range (blue: 450 nm to red: 620 nm) when formed into a thin film.

Thus, the compound according to the present invention represented by general formula [1] has a wide band gap and low absorption in the visible light range when formed into a thin film and thus is suitable for use as a constituent material of an organic photoelectric conversion element. In particular, the compound is preferably used as a layer in contact with an electrode.

The absorption spectra were measured using a V-560 manufactured by JASCO Corporation as a measuring device. The solution sample was measured using a quartz cell, and the deposited film sample used for the measurement was formed by deposition on a quartz substrate at a degree of vacuum of $5 \times 10^{-4}$ Pa or less.

(3) Having High Hole Transportability

To achieve high external quantum efficiency in an organic photoelectric conversion element, charges generated in a photoelectric conversion layer are preferably transported rapidly to an electrode. For example, holes generated in the photoelectric conversion layer reach a cathode after passing through, for example, an electron blocking layer. As described above, the electron blocking layer preferably has a sufficiently large thickness to sufficiently suppress electron injection from the electrode.

That is, the electron blocking layer, while having a sufficiently large thickness, is preferably able to transport holes generated in the photoelectric conversion layer rapidly to the cathode.

The organic compound according to the present invention has a benzene ring substituted with $Ar_3$ and $Ar_4$, as represented by general formula [1]. $Ar_3$ and $Ar_4$ each have a carbazolyl group. That is, the organic compound according to the present invention has a molecular structure whose both ends are terminated with a carbazolyl group, which has high hole transportability, and thus has high hole transportability. Thus, the organic compound according to the present invention can be suitably used for an electron blocking layer of an organic photoelectric conversion element.

(4) Having High Electron Blocking Ability

To suppress charge injection from an electrode and reduce dark current in an organic photoelectric conversion element, the injection barrier between the electrode and a charge blocking layer is preferably sufficiently large. For example, an electron blocking layer disposed between a photoelectric conversion layer and a cathode preferably has a low LUMO level to sufficiently suppress injection of electrons from the cathode.

The organic compound according to the present invention has a wide band gap, as described in (2). The organic compound according to the present invention has a low HOMO level because of having, in its molecular structure, two or more tert-butyl groups, which are alkyl groups having electron-donating properties. Therefore, the organic compound according to the present invention has a wide band gap and a low HOMO level. Consequently, the compound has a low LUMO level.

The LUMO level of the organic compound formed into a thin film can be calculated by subtracting an energy corresponding to an optical band gap calculated from an absorption spectrum from a HOMO level determined from an ionization potential.

A deposited film of exemplary compound A2 according to the present invention was formed by deposition on an AlN substrate at a degree of vacuum of $5 \times 10^{-4}$ Pa or less. The ionization potential of the film was measured using an AC-3 manufactured by Riken Keiki Co., Ltd. to be 6.09 eV.

As described above, the optical band gap was 3.36 eV, and thus the LUMO level can be estimated to be 2.73 eV, indicating that the film sufficiently functions as an electron blocking layer. Comparative compound 2 (compound 1-A disclosed in PTL 2) was subjected to the same measurement, and its LUMO level was calculated to be 2.93 eV. These values show that comparative compound 2 has lower electron blocking ability than exemplary compound A2 according to the present invention.

Thus, the organic compound according to the present invention has high electron blocking ability and can be suitably used for an electron blocking layer of an organic photoelectric conversion element.

(5) Having High Thermal Stability

In an organic photoelectric conversion element, thermal stability is required under high-temperature conditions during a process for forming a color filter and a process for mounting a photosensor, for example, a wire bonding process. Being thermally stable means not being thermally decomposed and staying amorphous under high-temperature conditions. To stay amorphous, it is preferable to have a high glass transition temperature. The glass transition temperature of an organic compound depends greatly on its molecular weight. Thus, one possible way to design an organic compound having a high glass transition temperature sufficient to withstand high-temperature processes is to increase the molecular weight of the organic compound.

However, increasing the molecular weight reduces sublimability, as described below. Thus, not all substituents may be incorporated, and it is preferable to select an appropriate substituent. The organic compound according to the present invention has at least two tert-butyl groups and thus has a high glass transition temperature and high sublimability.

The glass transition temperatures of exemplary compound A2 according to the present invention and comparative compound 2 were evaluated by differential scanning calorimetry (DSC). In the DSC, a sample of about 2 mg was placed in an aluminum pan, and the pan is then sealed and rapidly cooled from a high temperature over the melting point to bring the sample into an amorphous state, after which the temperature was raised at a rate of 10° C./min, thereby determining the glass transition temperature. A Pyris1 DSC manufactured by PerkinElmer Inc. was used as a measuring device.

The measurement revealed that exemplary compound A2 had a glass transition temperature of 200° C. and comparative compound 2 had a glass transition temperature of 160° C. The glass transition temperatures of the compounds are shown in Table 1 together with their decomposition temperatures and sublimation temperatures.

Thus, the organic compound according to the present invention has high thermal stability and can sufficiently withstand the process for mounting a photosensor. Using this compound can provide a stable organic photoelectric conversion element that can maintain its element properties after being subjected to a high-temperature process.

(6) Having High Sublimability

In an organic photoelectric conversion element, the purity of the organic compound is preferably increased by sublimation purification. This is because if the organic compound contains impurities, traps and free carriers derived from the impurities cause, for example, a local leakage current, leading to an increase in dark current.

The organic compound according to the present invention has high sublimability. This will be described. A compound obtained by replacing tert-butyl groups of exemplary compound A2 according to the present invention with phenyl groups is used as comparative compound 3. Comparative compound 3 has a molecular weight of 1017.26 and thus can be considered to have a high glass transition temperature and high thermal stability.

Exemplary compound A2 according to the present invention, comparative compound 2, and comparative compound 3 were each subjected to sublimation purification.

In the operation of sublimation purification, the temperature was gradually raised at a degree of vacuum of $1 \times 10^{-1}$ Pa under a flow of Ar to initiate sublimation purification. The sublimation temperature is a temperature at which a sufficient sublimation rate is reached.

Exemplary compound A2 sublimed at 410° C. That is, the sublimation temperature of A2 is 410° C. In the case of comparative compound 3, a partial sublimate was yielded at 470° C., but a decrease in purity due to thermal decomposition occurred, resulting in unsuccessful sublimation purification. This is probably because the sublimation temperature and the thermal decomposition temperature of comparative compound 3 are close to each other.

Thus, exemplary compound A2 according to the present invention and comparative compounds 2 and 3 were subjected to TG/DTA measurement. The decomposition temperature is a temperature at which the weight loss reaches 5%. Exemplary compound A2 according to the present invention had a decomposition temperature of 480° C. Comparative compounds 2 and 3 had a decomposition temperature of 480° C.

Exemplary compound A2 has a temperature difference between sublimation temperature and decomposition temperature of 70° C., whereas comparative compound 3 has a temperature difference of 10° C. The temperature difference of comparative compound 3 is small. That is, comparative compound 3, whose sublimation temperature and thermal decomposition temperature are close to each other, is a material unsuitable as a constituent material of an organic photoelectric conversion element.

Therefore, the organic compound according to the present invention has a large difference between sublimation temperature and thermal decomposition temperature because of having 2 or more tert-butyl groups, and the purity of the compound can be increased by sublimation purification.

TABLE 1

| | Structure | Glass transition temperature | Sublimability Decomposition temperature-sublimation temperature | Evaluation |
|---|---|---|---|---|
| Exemplary compound A2 | 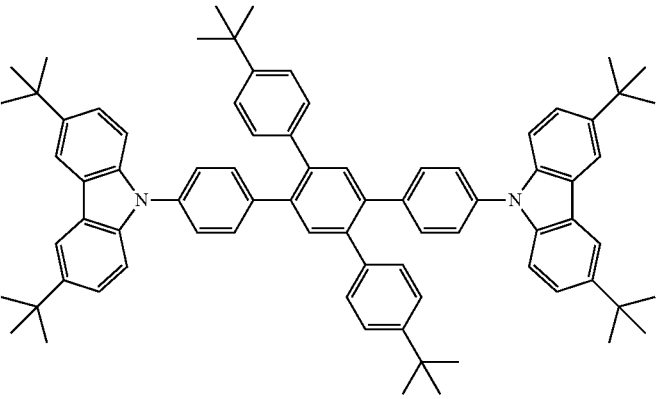 [SMILES: CC(C)(C)c1ccc(-c2cc(-c3ccc(-n4c5ccc(C(C)(C)C)cc5c5cc(C(C)(C)C)ccc54)cc3)c(-c3ccc(C(C)(C)C)cc3)cc2-c2ccc(-n3c4ccc(C(C)(C)C)cc4c4cc(C(C)(C)C)ccc43)cc2)cc1] | 200° C. | 480° C.-410° C. | Sublimable |
| Comparative compound 2 | 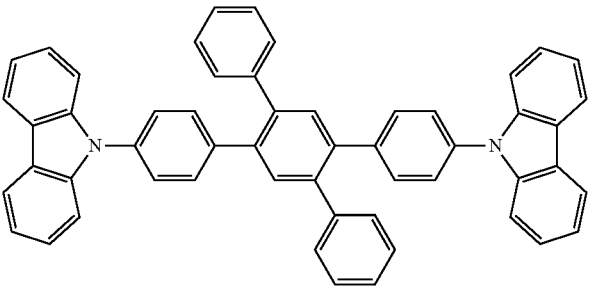 [SMILES: c1ccc(-c2cc(-c3ccc(-n4c5ccccc5c5ccccc54)cc3)c(-c3ccccc3)cc2-c2ccc(-n3c4ccccc4c4ccccc43)cc2)cc1] | 160° C. | 480° C.-380° C. | Sublimable |
| Comparative compound 3 | 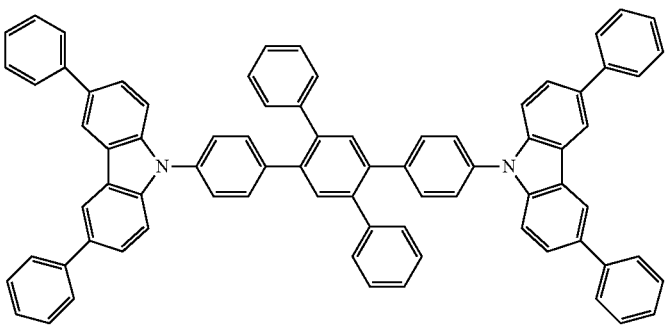 [SMILES: c1ccc(-c2ccc3c(c2)c2cc(-c4ccccc4)ccc2n3-c2ccc(-c3cc(-c4ccccc4)c(-c4ccc(-n5c6ccc(-c7ccccc7)cc6c6cc(-c7ccccc7)ccc65)cc4)cc3-c3ccccc3)cc2)cc1] | 200° C. | 480° C.-470° C. | Unsublimable |

Therefore, the organic compound according to the present invention has the above characteristics (1) to (6) and thus has higher sublimability and a higher glass transition temperature than comparative compounds 1 to 3. The organic compound according to the present invention can be suitably used for an organic photoelectric conversion element. In particular, the compound of general formula [1] can be suitably used for an electron blocking layer.

When the compound of general formula [1] is used for an organic layer of an organic photoelectric conversion element, the layer containing the compound of general formula [1] may be formed, for example, by a spin coating method, but preferably by deposition under vacuum (a vacuum deposition method). This is because the vacuum deposition method can form a high-purity thin film. When the vacuum deposition method is used, the required temperature typically increases as the molecular weight of the organic compound used as a constituent material of the layer increases. When the required temperature reaches an excessively high decomposition temperature, the organic compound used as a constituent material is likely to undergo thermal decomposition.

Examples of Organic Compounds According to Present Invention

Specific examples of the compound of general formula [1] are shown below. It should be noted that, in the present invention, the compound of general formula [1] is not limited to these specific examples.

A1
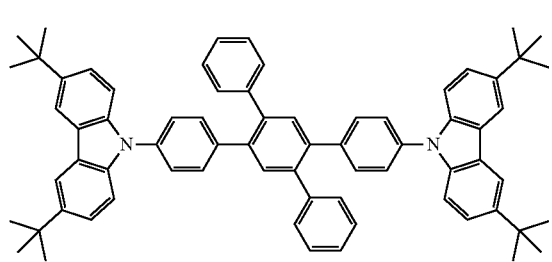
A2
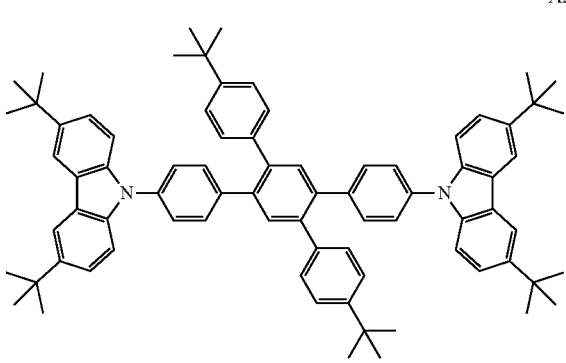
A3
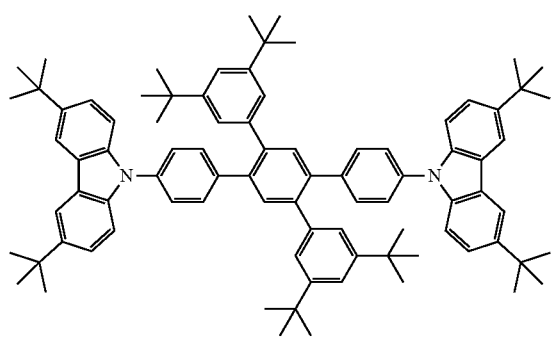
A4
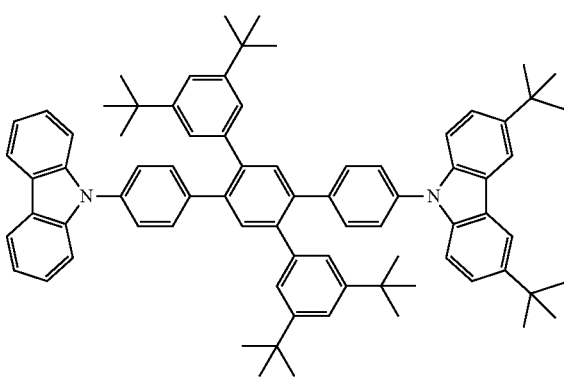
A5
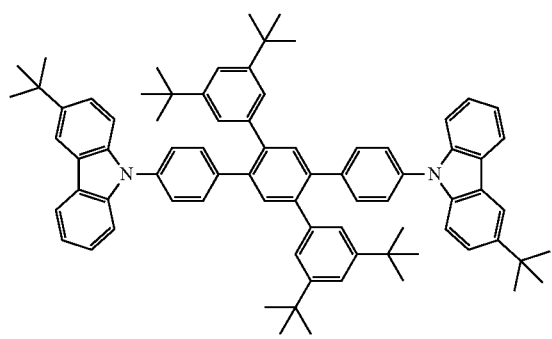
A6
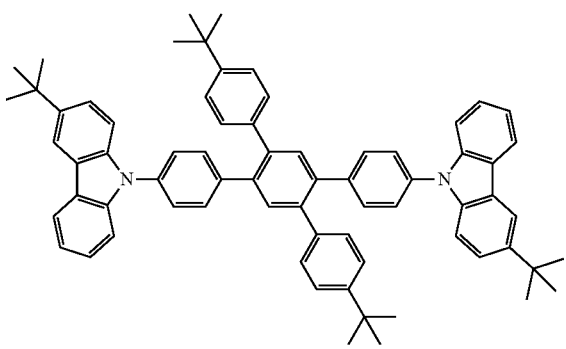
A7
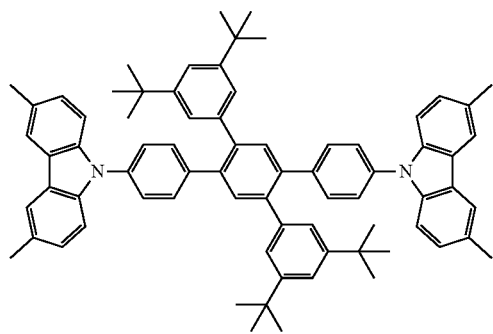
A8
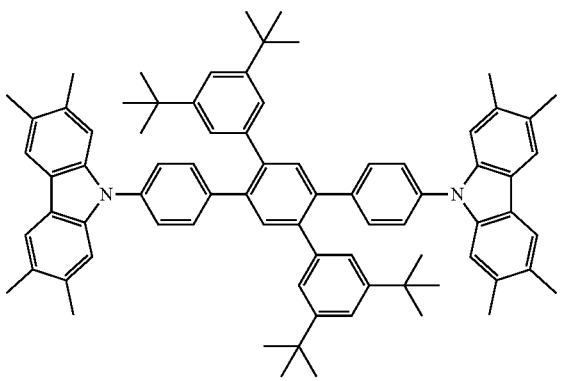

-continued
A9
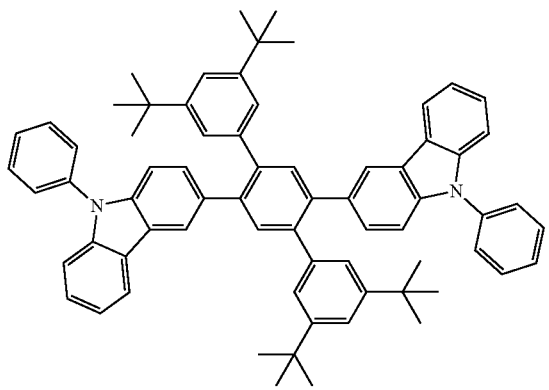
A10
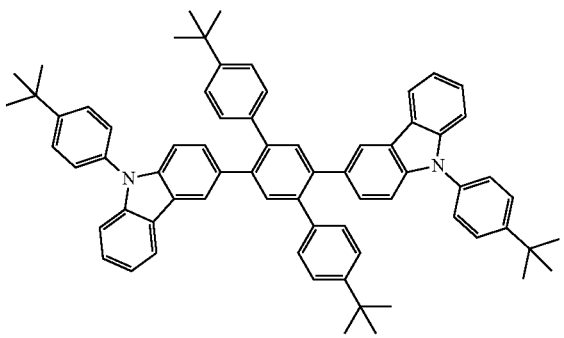
A11
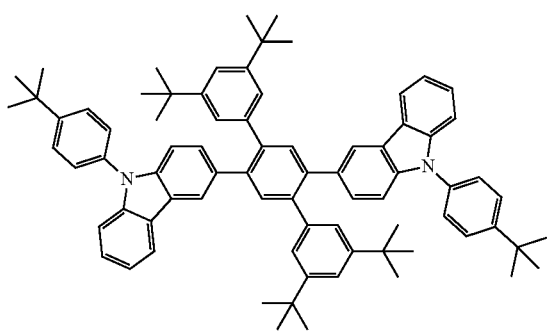
A12
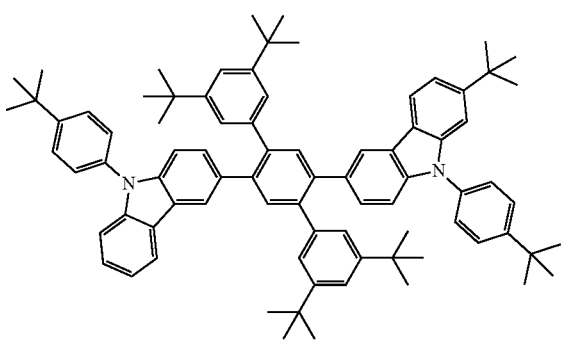
A13
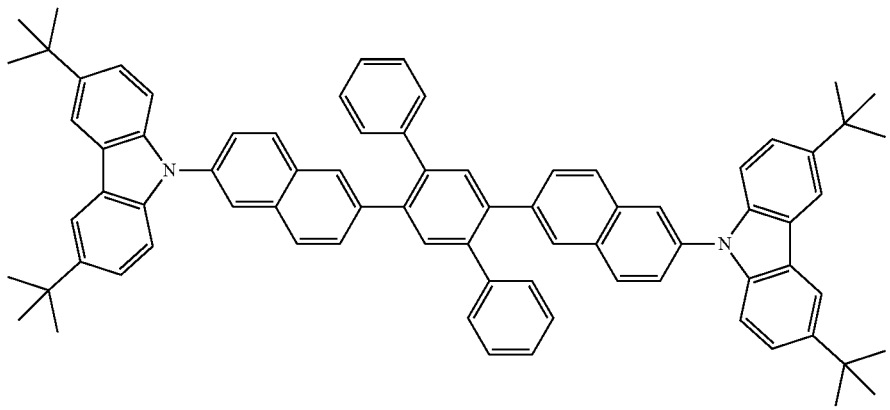
A14
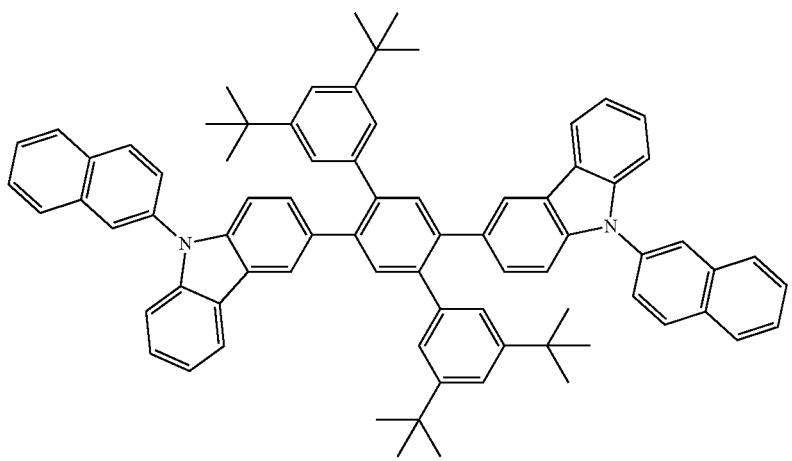

-continued
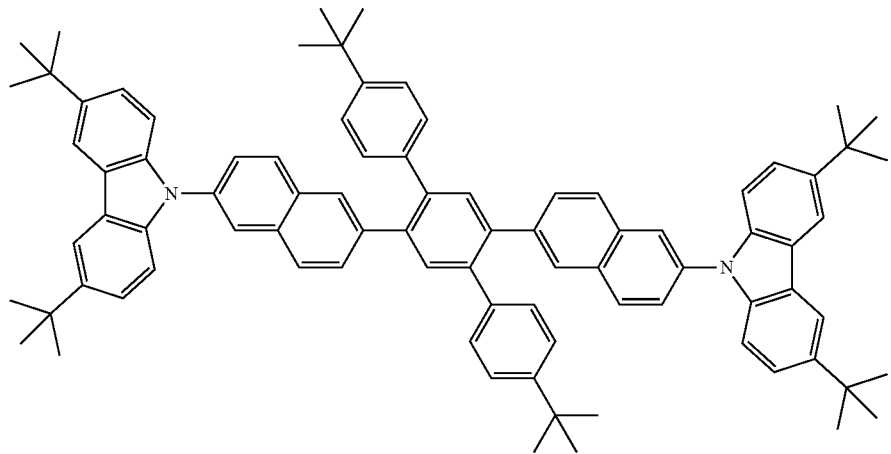
A15
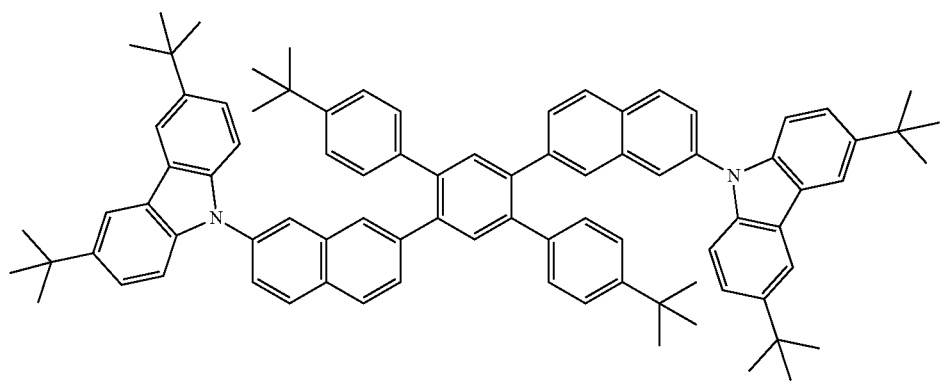
A16
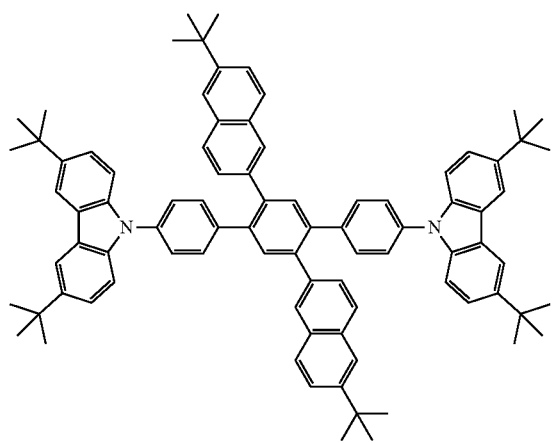
A17
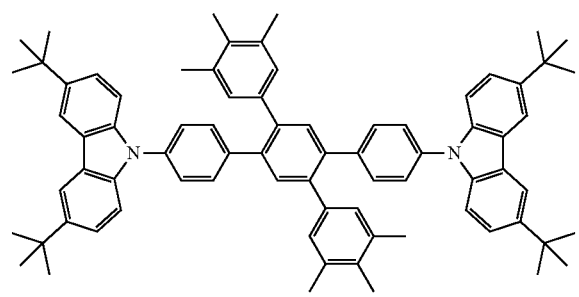
A18

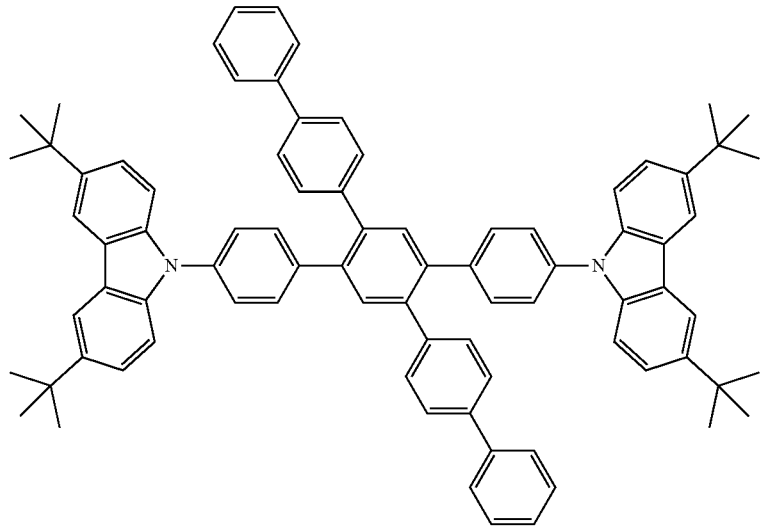
A19
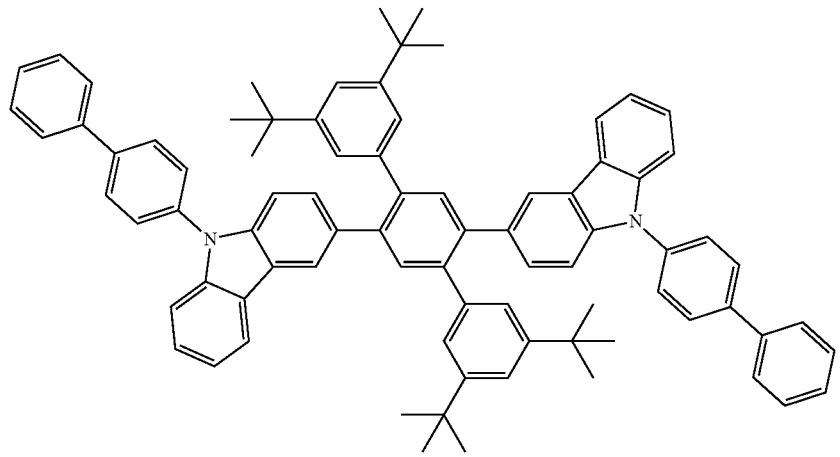
A20
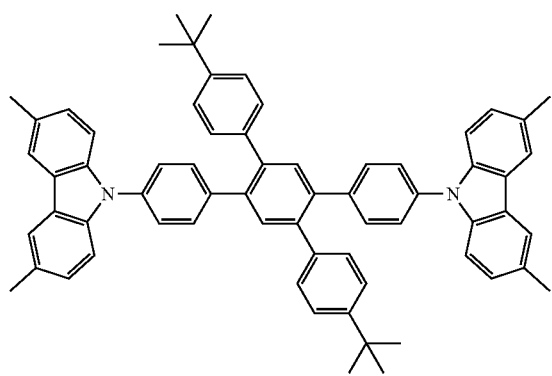
A21
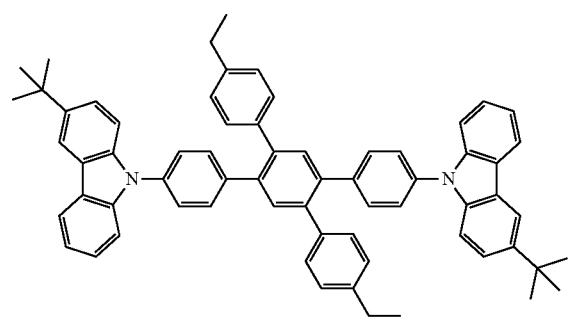
A22

-continued
A23
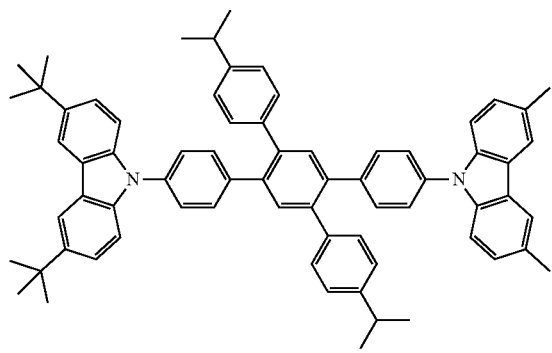
A24
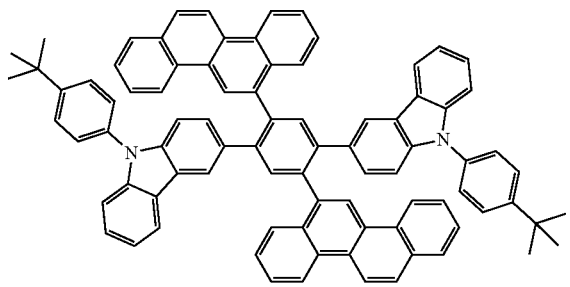
A25
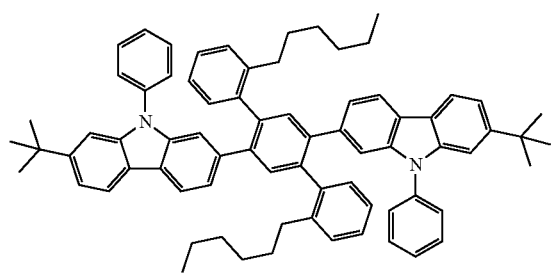
A26
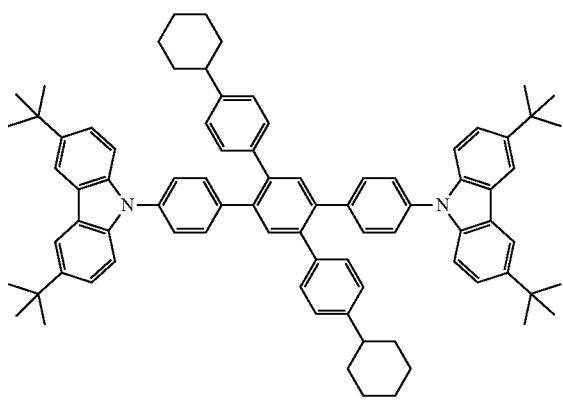
A27
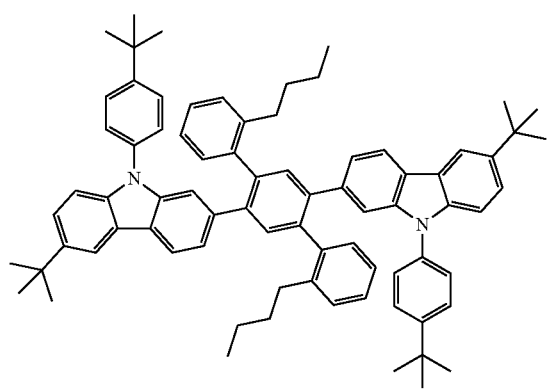
A28
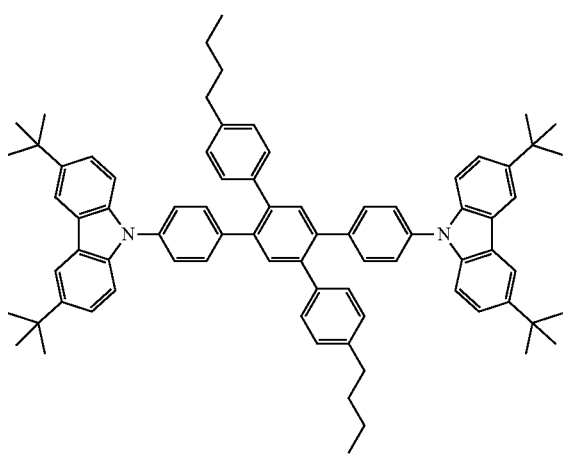

-continued
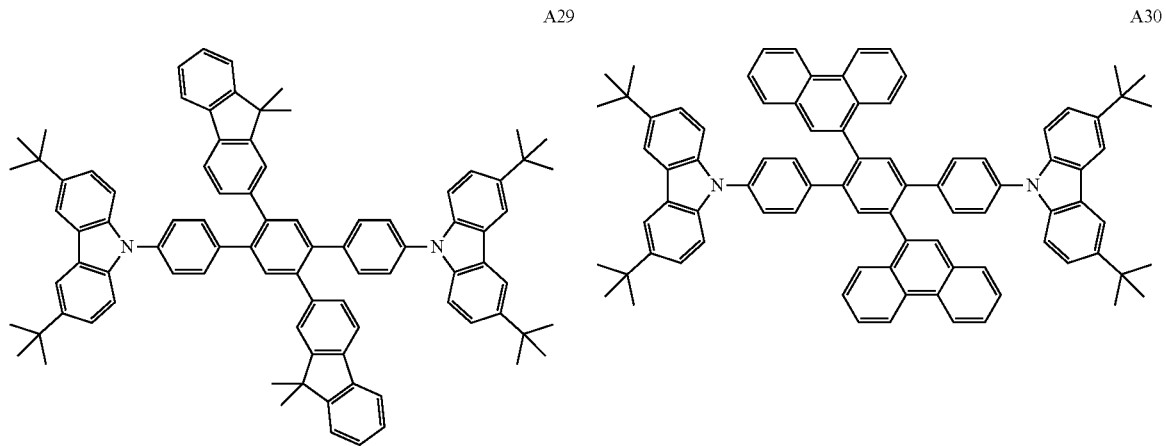
A29 A30
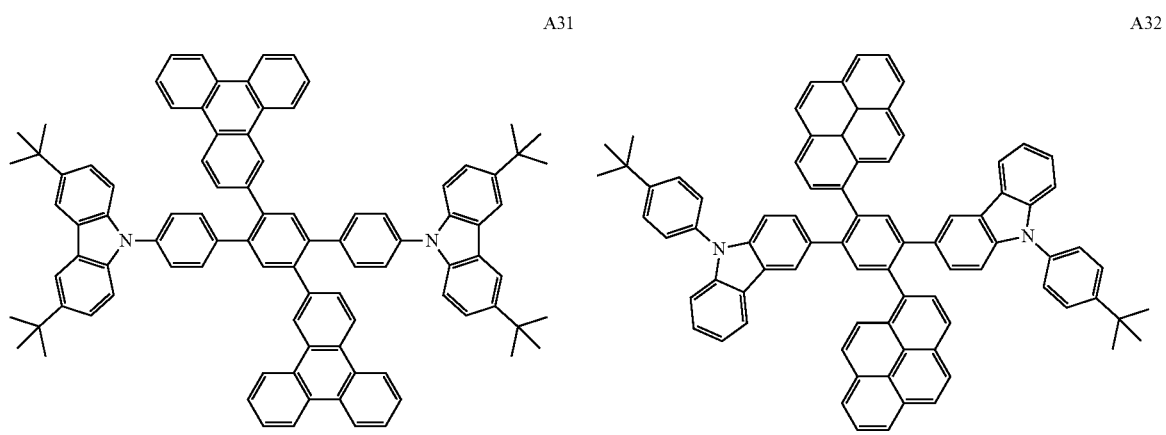
A31 A32
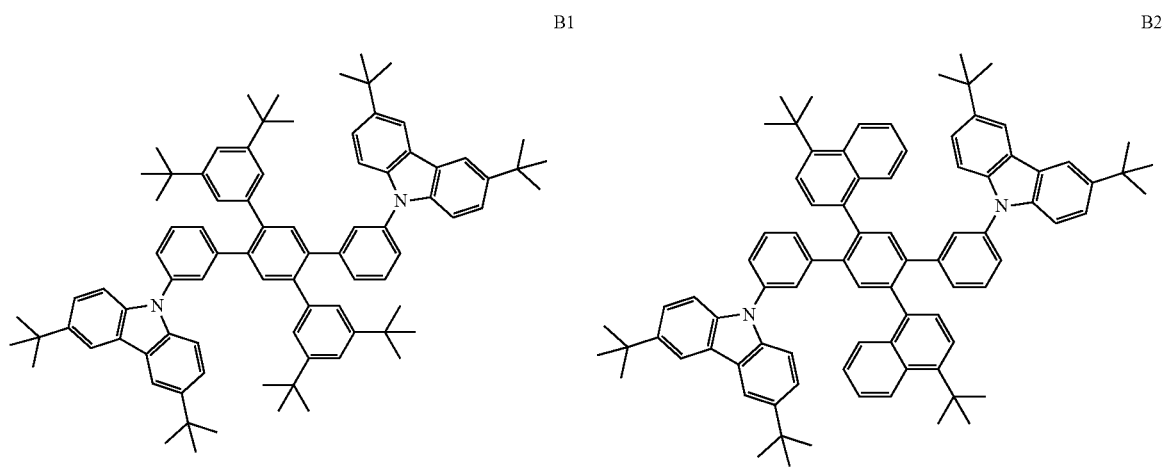
B1 B2

-continued
B3
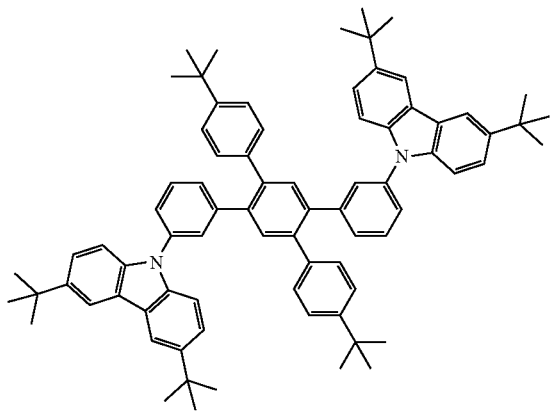
B4
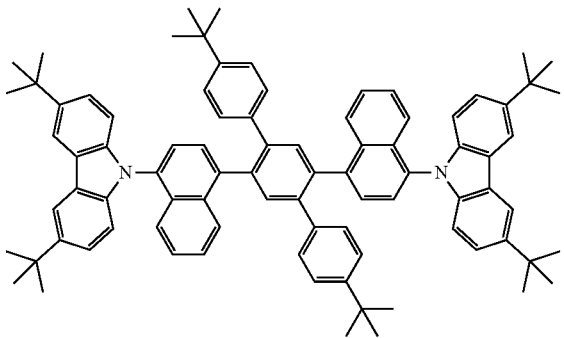
B5
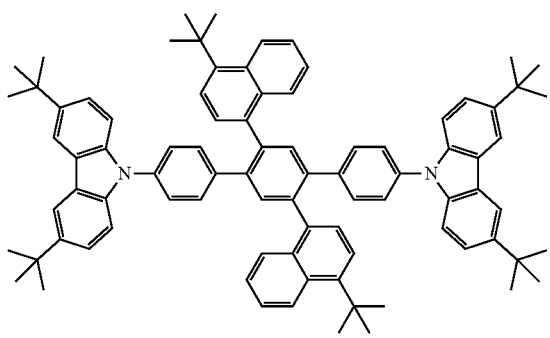
B6
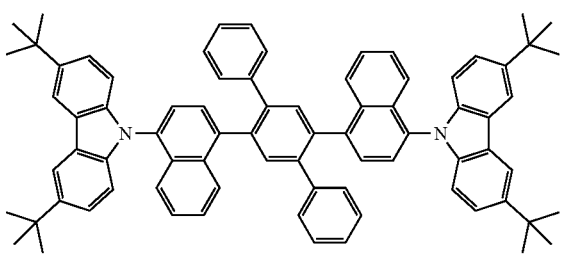
B7
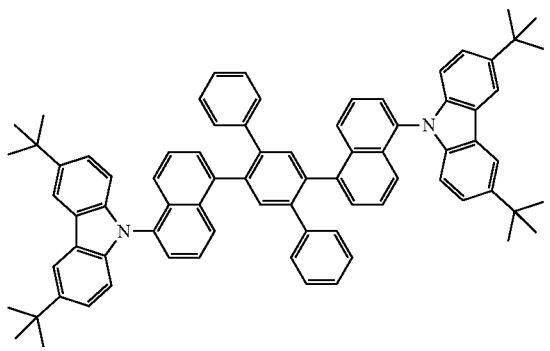
B8
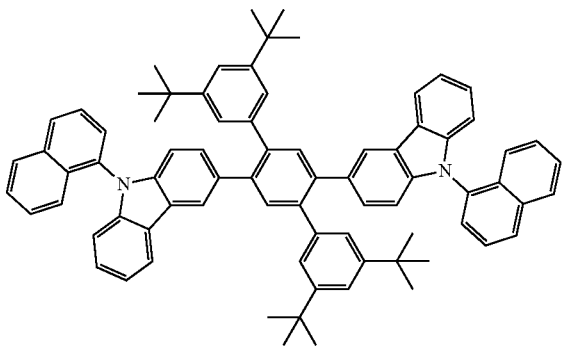
B9
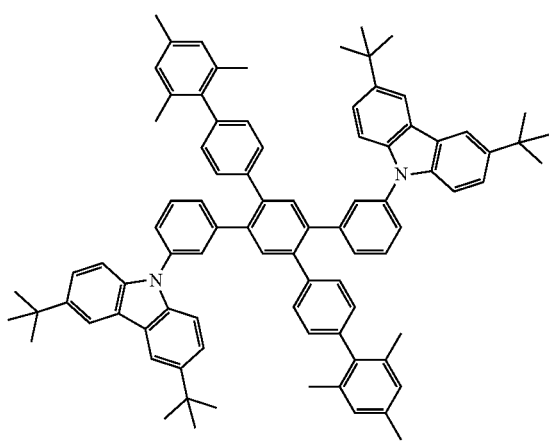
B10
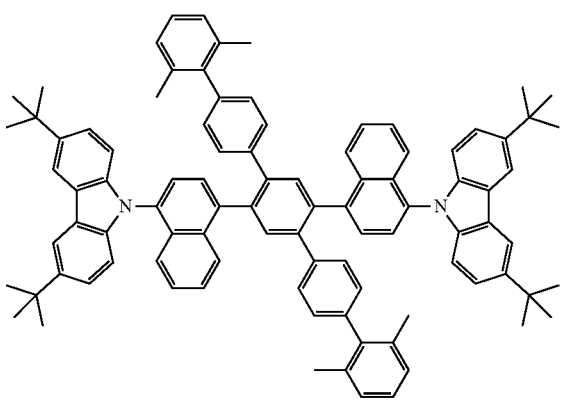

-continued
B11
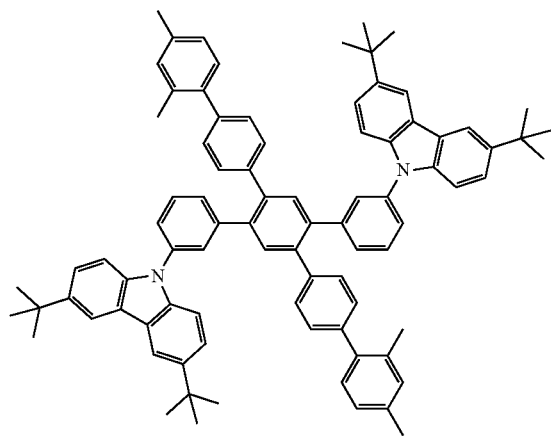
B12
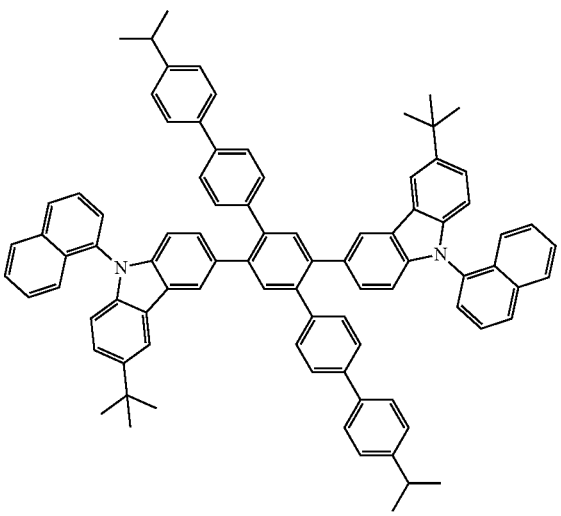
C1
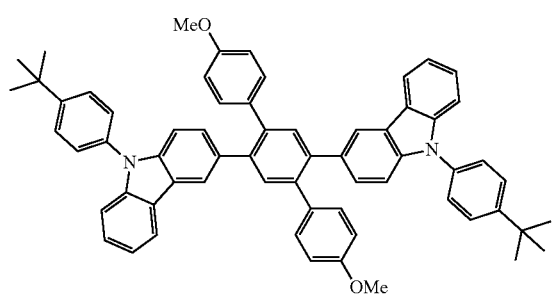
C2
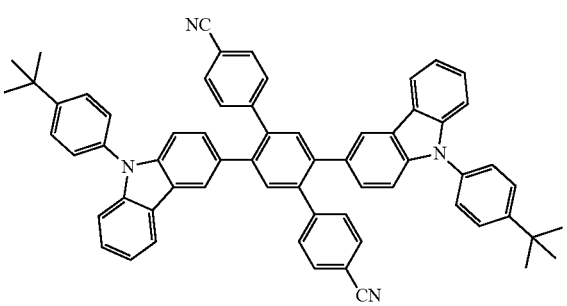
C3
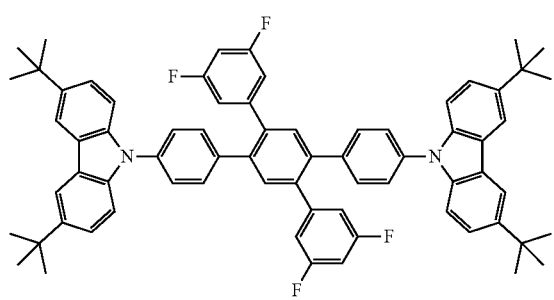
C4
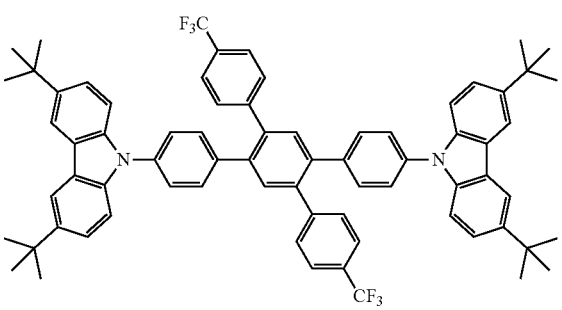
C5
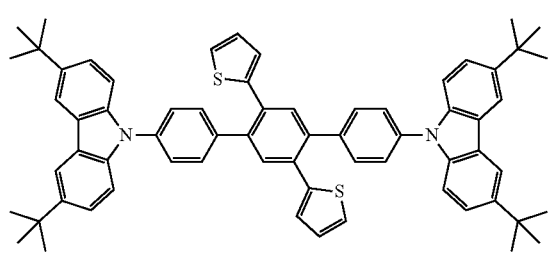
C6
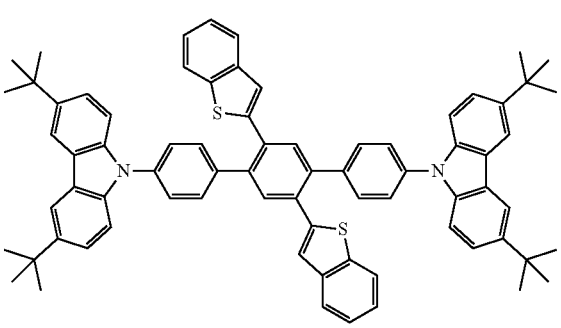

-continued
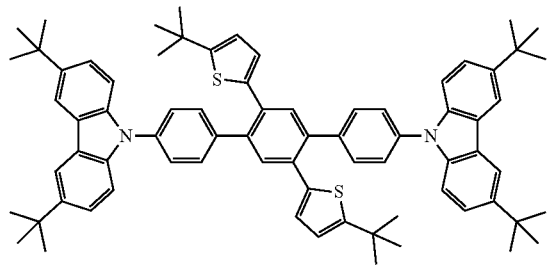
C7
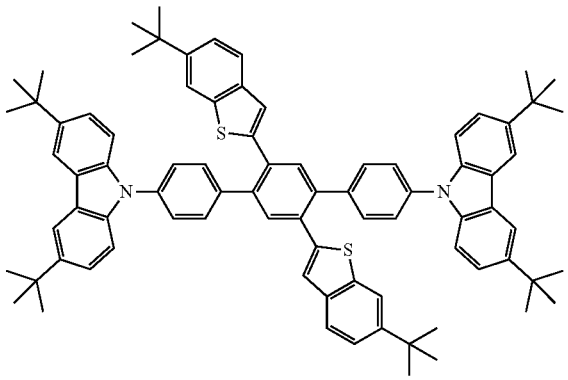
C8
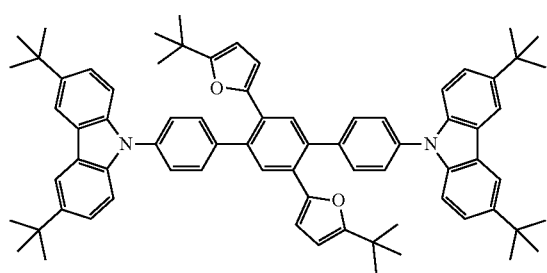
C9
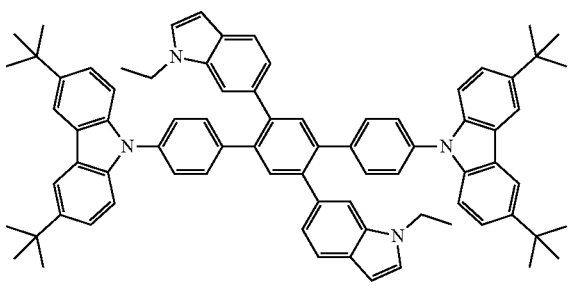
C10
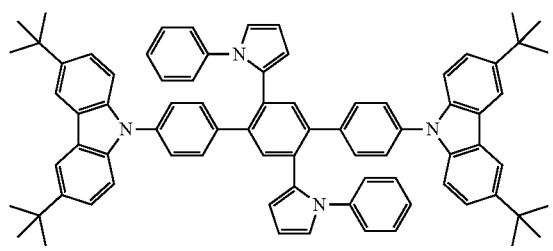
C11
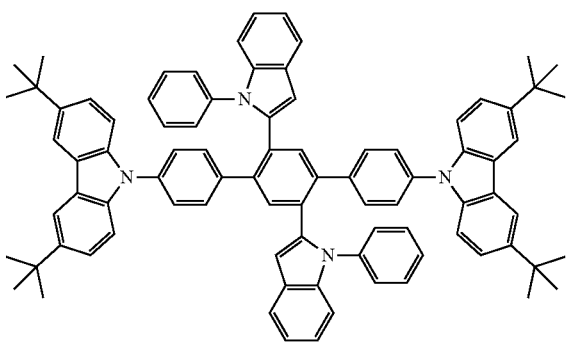
C12
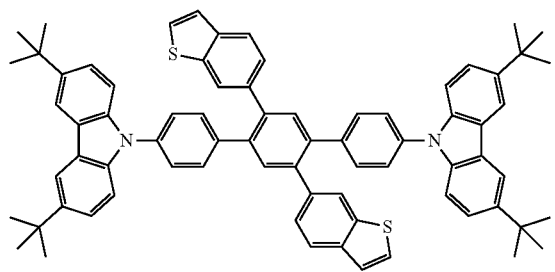
C13
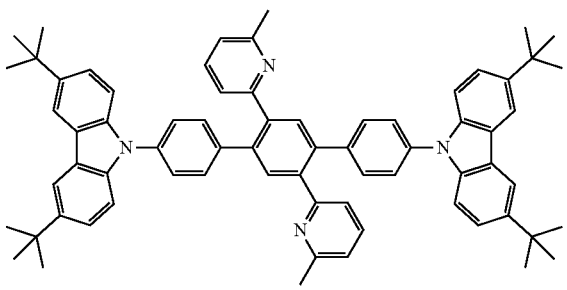
C14

-continued

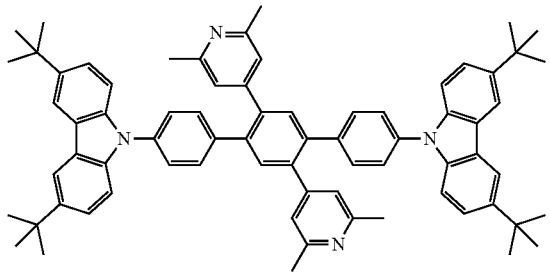

C15

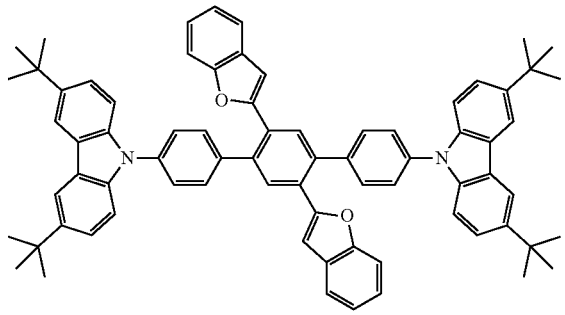

C16

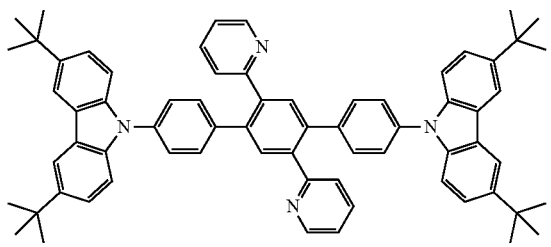

C17

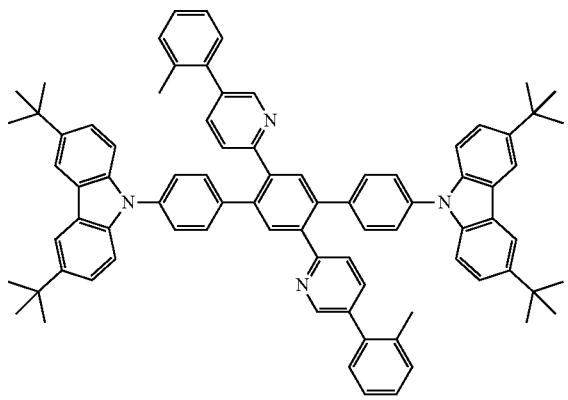

C18

Of the exemplary compounds, exemplary compounds of group A have a structure in which $Ar_1$ and $Ar_2$ in formula [1] are each a substituted or unsubstituted aromatic hydrocarbon group having 6 to 18 carbon atoms. Exemplary compounds of group A have high thermal stability and high sublimability because $Ar_1$ and $Ar_2$ are each an aromatic hydrocarbon group.

Exemplary compounds A1 to A12 have particularly high thermal stability and high sublimability because Ar and $Ar_2$ in formula [1] are each a phenyl group and $Ar_3$ and $Ar_4$ in formula [1] are each a substituent represented by general formula [2a].

Exemplary compounds A13 to A16 have high thermal stability because $Ar_3$ and $Ar_4$ in formula [1] are each a substituent represented by general formula [2b] or [2c].

Furthermore, exemplary compounds A25 to A28 have various alkyl groups, particularly, a linear alkyl group (e.g., n-butyl) or a cycloalkyl group (e.g., cyclohexyl), and thus have high solubility. In other words, these compounds have a linear or cyclic alkyl group having 4 or more carbon atoms. Thus, these compounds are suitable for use in forming a film by coating.

Exemplary compounds of group B have a structure in which at least one of $Ar_1$ to $Ar_4$ in formula [1] is bonded to a meta position of a benzene skeleton or a peri position of a naphthalene skeleton. Thus, the whole molecular structure of these compounds is greatly twisted. That is, exemplary compounds of group B are particularly advantageous in that their molecular structure has many twisted portions due to the substitution position and thus a highly amorphous organic compound layer is formed. The benzene skeleton is a concept including a benzene ring constituting a carbazolyl group. Exemplary compound B12, which has a bond at the 3-position of a carbazolyl group, is a compound in which the benzene ring in general formula [1] is bonded at a meta position of a benzene skeleton.

Exemplary compounds of group C have a structure in which at least one of $Ar_1$ and $Ar_2$ in formula [1] is a substituted or unsubstituted heteroaromatic group having 3 to 17 carbon atoms. When the heteroaromatic ring has a nitrogen atom, the compound itself has a high (or, a deep) oxidation potential because of the electron-withdrawing power of the nitrogen atom and thus is resistant to oxidation.

When the heteroaromatic ring has a sulfur atom or an oxygen atom, the compound has a strong intermolecular interaction because the sulfur atom and the oxygen atom have many unshared electron pairs, and thus the compound has high carrier transportability.

That is, exemplary compounds of group C are particularly advantageous in that the compounds have stability and carrier transportability due to the electronic effects. These compounds can also be used for a hole blocking layer.

Of the exemplary compounds, A1 to A20, A26 to A31, B1 to B12, and C3 to C18 are excellent in the above-described characteristics (1), (2), and (4) to (6) because the total number of tert-butyl groups is 4 or more. Thus, these compounds are suitable as a material for an organic photoelectric conversion element.

Of the exemplary compounds, A2 to A6, A10 to A12, A15 to A17, B1 to B5, and C7 to C9 are more excellent in the above-described characteristics because the total number of tert-butyl groups is 6 or more. Thus, these compounds are suitable for use.

Figure 3:
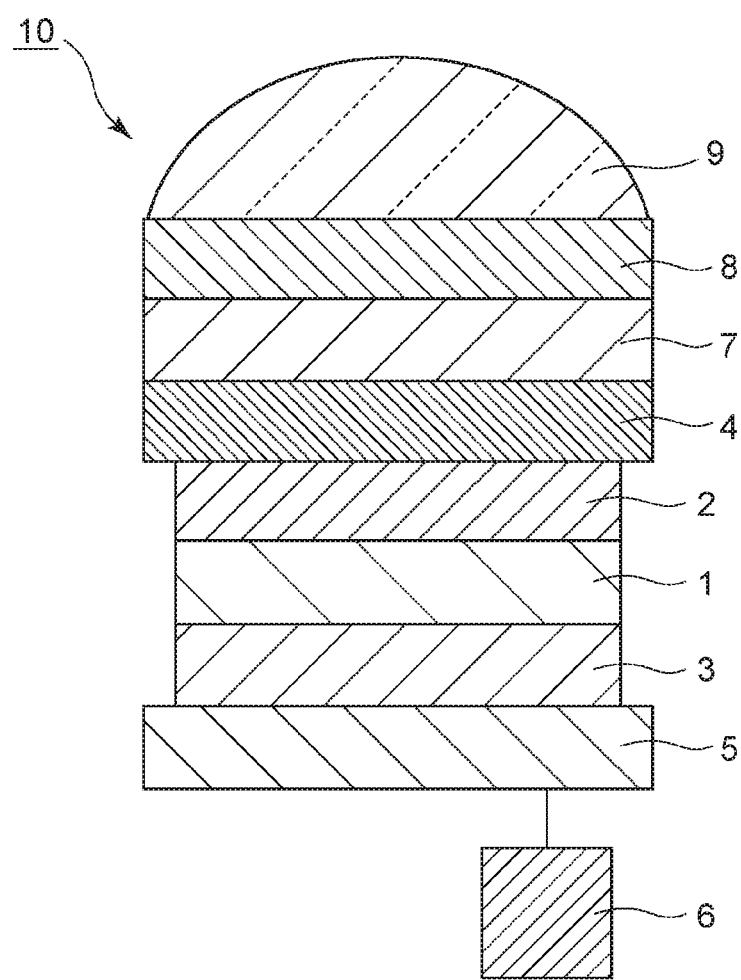
FIG. 3 is a schematic view of an example of an organic photoelectric conversion element according to an embodiment.

Photoelectric conversion element according to embodiment (1) Photoelectric Conversion Element FIG. 3 is a schematic sectional view of an example of a photoelectric conversion element according to an exemplary embodiment. The photoelectric conversion element includes an anode 5, a cathode 4, and a first organic compound layer 1 disposed therebetween. The first organic compound layer 1 forms a photoelectric conversion unit that converts light into charges. Hence, the first organic compound layer can also be called a photoelectric conversion layer.

When the photoelectric conversion element includes a plurality of layers, the plurality of layers are preferably stacked from the anode toward the cathode.

The photoelectric conversion element may further include a second organic compound layer 2 disposed between the first organic compound layer 1 and the cathode 4 and a third organic compound layer 3 disposed between the first organic compound layer 1 and the anode 5.

A protective layer 7 is disposed on the cathode. A wavelength selection unit 8 is disposed on the protective layer 7. A microlens 9 is disposed on the wavelength selection unit 8. A readout circuit 6 is connected to the anode. The photoelectric conversion element may be disposed on a substrate (not illustrated).

In the photoelectric conversion element, a voltage may be applied between the anode and the cathode when photoelectric conversion is performed. The voltage depends on the total thickness of the organic compound layers but is preferably about 1 V or more and 15 V or less, more preferably about 2 V or more and 10 V or less.

(2) Substrate

The organic photoelectric conversion element according to the present embodiment may include a substrate. Examples of substrates include glass substrates, flexible substrates, and semiconductor substrates.

The photoelectric conversion element according to the present embodiment may include a semiconductor substrate. The constituent elements of the semiconductor substrate are not limited as long as a charge accumulation unit and a floating diffusion (FD) can be formed by impurity implantation. Examples of such constituent elements include Si, GaAs, and GaP. In particular, Si is preferred.

The semiconductor substrate may be an N-type epitaxial layer. In this case, a P-type well, an N-type well, a P-type semiconductor region, and an N-type semiconductor region are formed in the semiconductor substrate.

The charge accumulation unit is an N-type or a P-type semiconductor region that is formed in the semiconductor substrate by ion implantation and that accumulates charges generated from the photoelectric conversion unit.

When electrons are accumulated, an N-type semiconductor region may be formed in a surface of the semiconductor substrate, or an accumulation diode having a P—N structure may be formed from the surface of the substrate. In both cases, electrons can be accumulated in the N-type semiconductor region.

When holes are accumulated, a P-type semiconductor region may be formed in the semiconductor substrate, or an accumulation diode having an N—P structure may be formed from the surface of the substrate. In both cases, holes can be accumulated in the P-type semiconductor region.

The accumulated charges are transferred from the charge accumulation unit to the FD. The charge transfer may be controlled by a gate electrode. The charges generated from the organic compound layers are accumulated in the charge accumulation unit, and the charges accumulated in the charge accumulation unit are transferred to the FD. The charges are then converted into current by an amplifier transistor, which will be described later.

When the charge accumulation unit has a P-N junction formed therein, photoelectric conversion may be performed with light leaking from the photoelectric conversion unit.

A charge output unit may be formed instead of the charge accumulation unit. When an output unit is formed, charges are transferred from the electrode to the amplifier transistor and others not via the FD.

(3) Anode

The anode is an electrode that collects electrons of charges generated from the photoelectric conversion layer. In an image pickup element, the anode may be a pixel electrode. The anode may be disposed closer to a pixel circuit than the cathode is to the pixel circuit. The anode, because of its function, can also be called an electron collecting electrode.

Examples of constituent materials of the anode include ITO, indium zinc oxide, $SnO_2$, antimony-doped tin oxide (ATO), ZnO, Al-doped zinc oxide (AZO), gallium-doped zinc oxide (GZO), $TiO_2$, and fluorine-doped tin oxide (FTO)

(4) Cathode

The cathode is an electrode that collects holes of charges generated from the photoelectric conversion layer. In an image pickup element, the cathode may be a pixel electrode.

Specific examples of constituent materials of the cathode include metals, metal oxides, metal nitrides, metal borides, organic conductive compounds, and mixtures thereof. More specific examples include conductive metal oxides such as antimony-doped tin oxide (ATO), fluorine-doped tin oxide (FTO), tin oxide, zinc oxide, indium oxide, indium tin oxide (ITO), and indium zinc oxide; metal materials such as gold, silver, magnesium, chromium, nickel, titanium, tungsten, and aluminum; conductive compounds such as oxides and nitrides of these metal materials (e.g., titanium nitride (TiN)); mixtures and laminates of these metals and conductive metal oxides; inorganic conductive materials such as copper iodide and copper sulfide; organic conductive materials such as polyaniline, polythiophene, and polypyrrole; and laminates of these materials and ITO or titanium nitride. Particularly preferably, the constituent material of the cathode is a material selected from a magnesium-silver alloy, titanium nitride, molybdenum nitride, tantalum nitride, and tungsten nitride.

The pixel electrode may be an anode or a cathode. The electrode on the light-emission side preferably has high transparency, specifically, 80% or more.

The electrode on the light incident side can also be called the upper electrode. In this case, the other is called the lower electrode.

The above-described two electrodes (the anode and the cathode) can each be formed by a method appropriately selected in consideration of suitableness for electrode materials used. Specifically, for example, wet methods such as printing methods and coating methods; physical methods such as vacuum deposition methods, sputtering methods, and ion plating methods; and chemical methods such as CVD and plasma CVD methods can be used.

When ITO is used to form the electrodes, the electrodes can be formed, for example, by an electron beam method, a sputtering method, a resistance heating deposition method, a chemical reaction method (e.g., a sol-gel method), or application of a dispersion of indium tin oxide.

In this case, the surfaces of the electrodes (ITO electrodes) formed may be subjected to UV-ozone treatment, plasma treatment, or other treatment.

When TiN is used to form the electrodes, various film-forming methods including reactive sputtering methods can be used. In this case, the electrodes (TiN electrodes) formed may be subjected to annealing treatment, UV-ozone treatment, plasma treatment, or other treatment.

(5) First Organic Compound Layer

The first organic compound layer can also be called a photoelectric conversion layer, as described above. Constituent materials of the photoelectric conversion layer of the organic photoelectric conversion element according to the present embodiment will be described. The photoelectric conversion layer preferably has high light absorptivity and efficiently effects charge separation of received light, that is, preferably offers high photoelectric conversion efficiency.

The photoelectric conversion layer is preferably able to transport generated charges, that is, electrons and holes, rapidly to the electrodes. To prevent degradation of film quality, such as crystallization, the photoelectric conversion layer is preferably made of a material having a high glass transition temperature. For higher film quality, the photoelectric conversion layer may be a layer of a mixture with a material having a high glass transition temperature.

The first organic compound layer may contain a plurality of organic compounds. When the first organic compound layer contains a plurality of organic compounds, a mixture of the plurality of organic compounds may be contained in a single layer, or the plurality of organic compounds may be contained in a plurality of layers.

The first organic compound layer preferably contains a p-type organic semiconductor or an n-type organic semiconductor, more preferably contains, as at least a part thereof, a bulk heterojunction layer (mixed layer) in which an organic p-type compound and an organic n-type compound are mixed together.

The presence of the bulk heterojunction layer in the first organic compound layer can provide improved photoelectric conversion efficiency (sensitivity). The presence of the bulk heterojunction layer in an optimum proportion can increase the electron mobility and the hole mobility of the first organic compound layer 1 to increase the photoresponse speed of the photoelectric conversion element.

The first organic compound layer preferably contains, as the n-type organic semiconductor, fullerene or a fullerene analogue. Electron paths are formed by fullerene molecules or fullerene analogue molecules, thus improving electron transportability to improve the responsiveness of the photoelectric conversion element.

The fullerene content or the fullerene analogue content is preferably 20 vol % or more and 80 vol % or less, provided that the total volume of the photoelectric conversion layer is 100 vol %.

The term "fullerene analogue" is the generic name of closed-shell hollow clusters consisting only of many carbon atoms. Examples thereof include C60 and higher-order fullerenes such as C70, C74, C76, and C78. These materials may be used alone or in combination. As a material used for charge separation and electron transport, other different materials may be used together with the fullerene analogues. Examples of materials other than fullerene include naphthalene compounds such as NTCDI, perylene compounds such as PTCDI, phthalocyanine compounds such as SubPc, and thiophene compounds such as DCV3T, which are known as n-type organic semiconductors.

Examples of fullerene analogues include fullerene C60, fullerene C70, fullerene C76, fullerene C78, fullerene C80, fullerene C82, fullerene C84, fullerene C90, fullerene C96, fullerene C240, fullerene 540, mixed fullerene, and fullerene nanotubes.

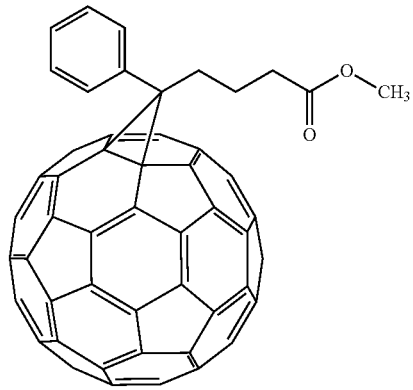
[60]PCBM

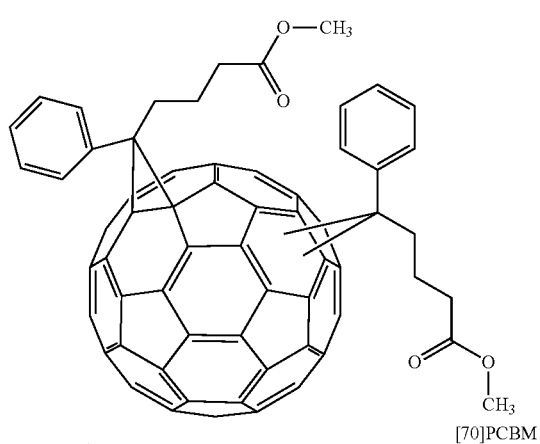
bis[60]PCBM

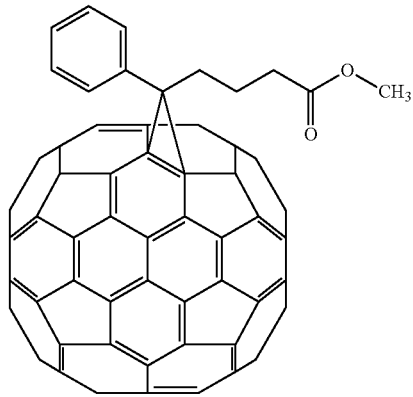
[70]PCBM

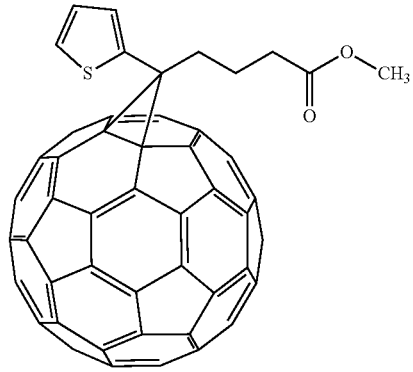
[60]ThCBM

Examples of p-type organic semiconductors contained in the photoelectric conversion element include the following organic compounds. The organic compounds represented by the following structural formulae may be substituted, for example, with an alkyl group as long as their function is not adversely affected.
CG1
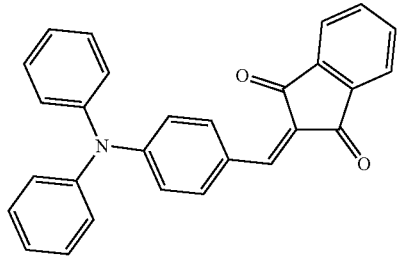
CG2
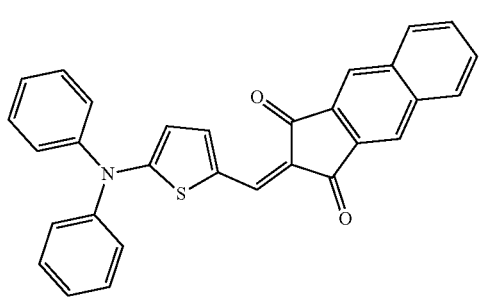
CG3
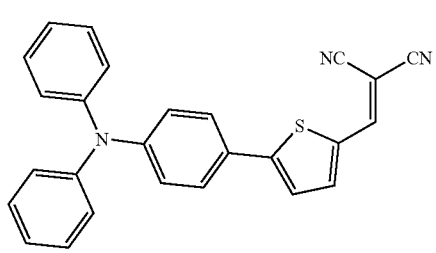
CG4
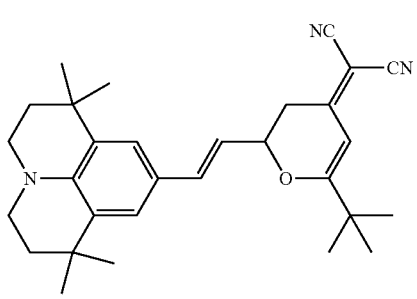
CG5
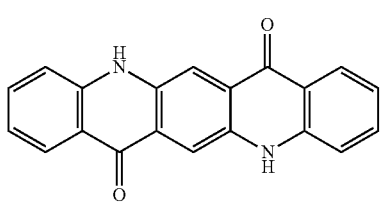
CG6
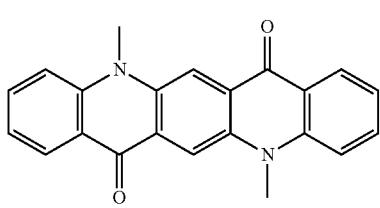
CG7
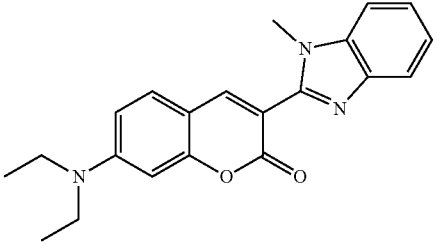
CG8
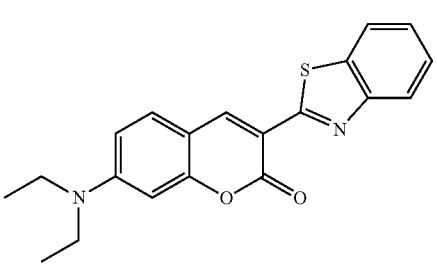
CG9
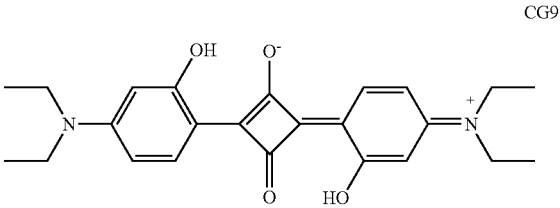
CG10
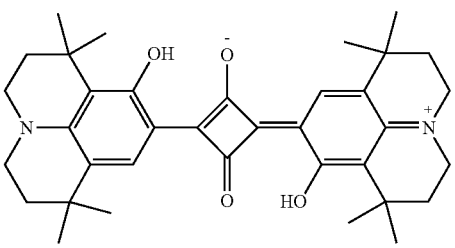
CG11
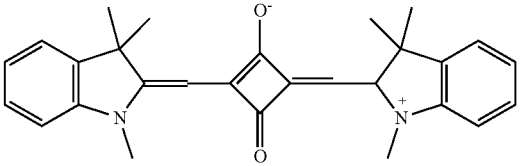
CG12
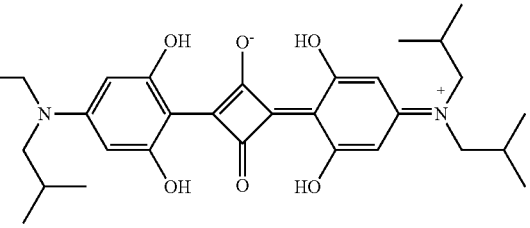

CG13
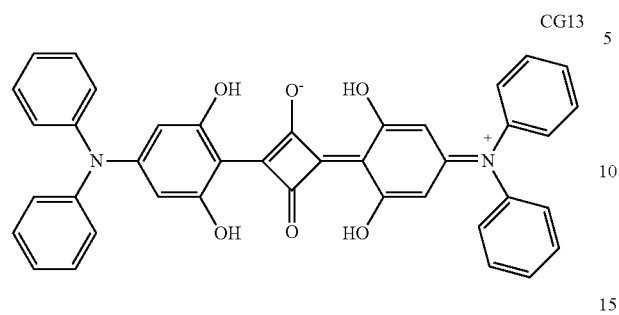
CG14
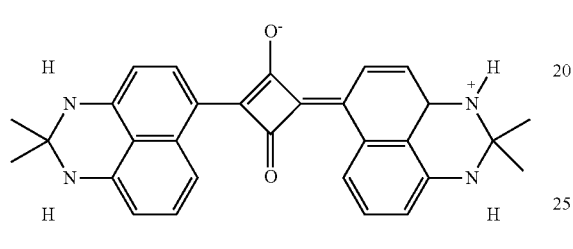
CG15
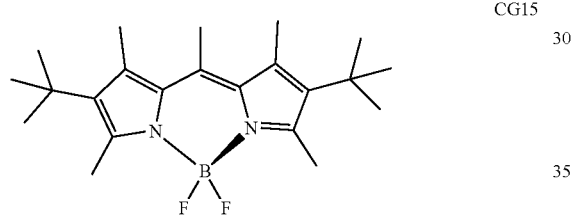
CG16
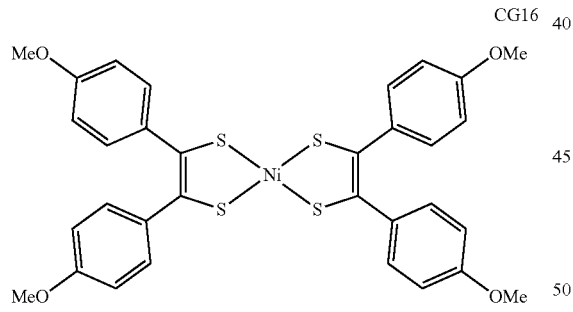
CG17
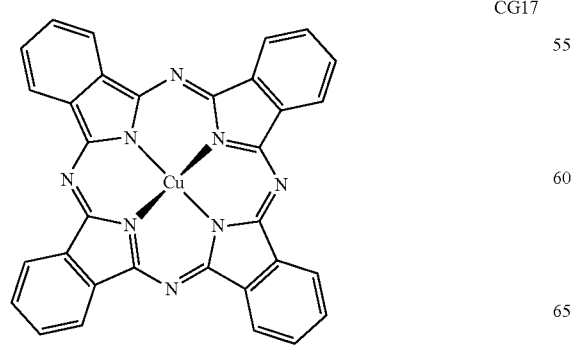
CG18
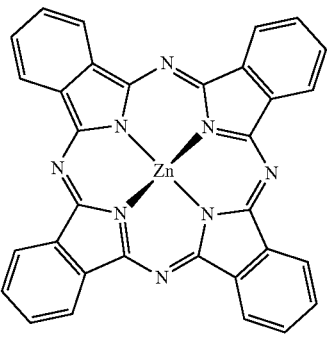
CG19
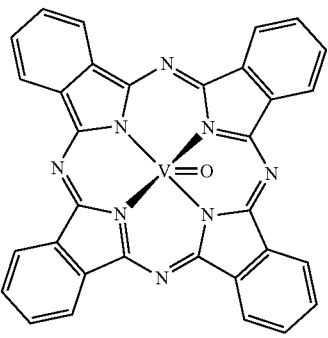
CG20
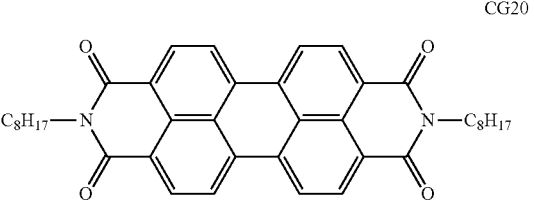
CG21
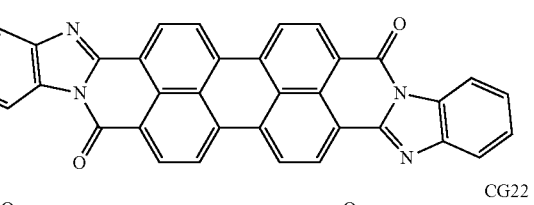
CG22
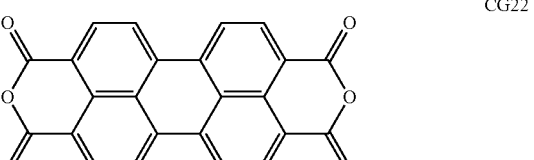
CG23
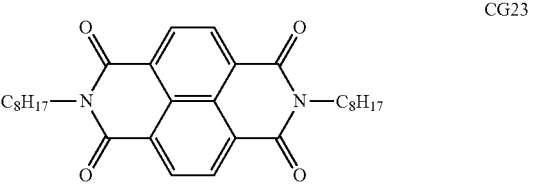
CG24
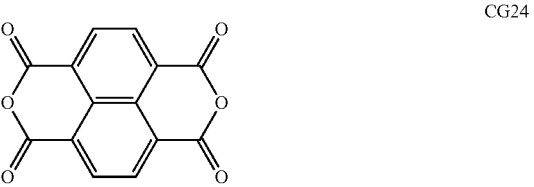

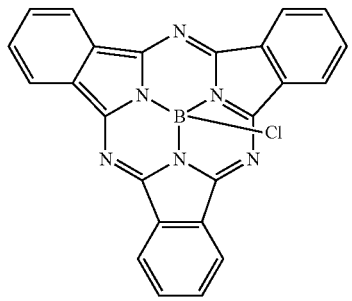
CG25

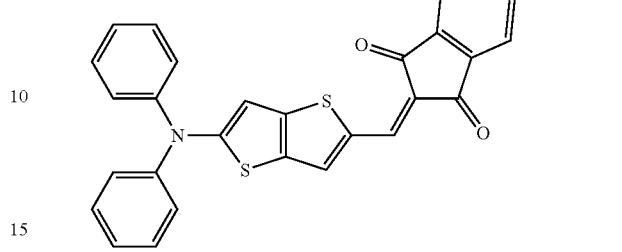
CG29

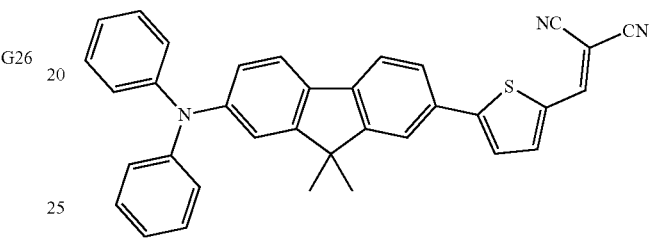
CG30

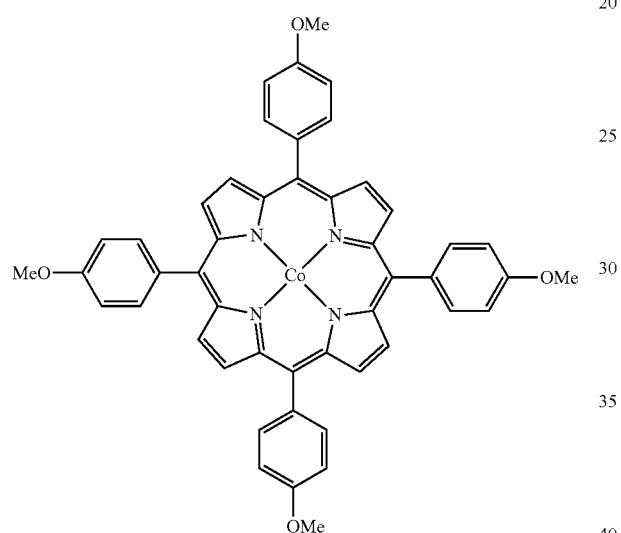
CG26

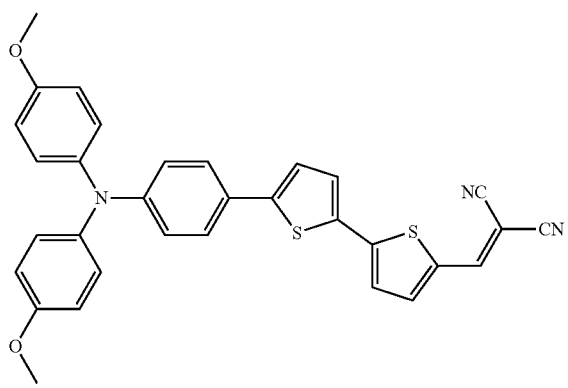
CG31

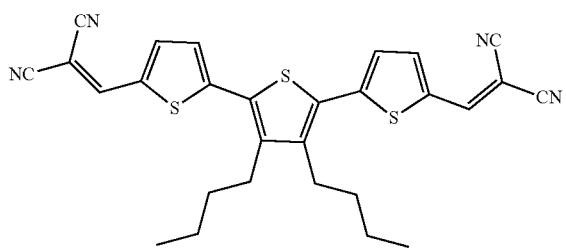
CG27

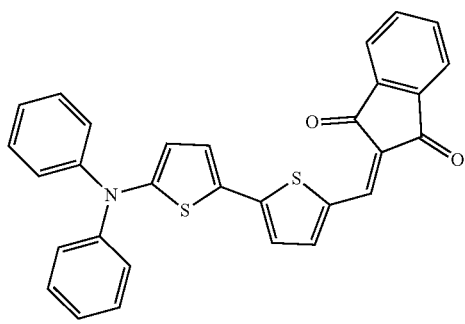
CG28

(6) Second Organic Compound Layer

The second organic compound layer inhibits electrons from entering the first organic compound layer from the cathode and preferably has a low electron affinity (close to the vacuum level). A low electron affinity can translate into a low LUMO level. The second organic compound layer, because of its function, can also be called an electron blocking layer. The second organic compound layer 2 may be formed of multiple layers or a bulk heterojunction layer (mixed layer).

The electron blocking layer preferably contains the organic compound according to the present invention. Other functional layers may be disposed between the cathode and the electron blocking layer.

(7) Third Organic Compound Layer

The third organic compound layer inhibits holes from entering the first organic compound layer from the anode and preferably has a high ionization potential (distant from the vacuum level). A high ionization potential can translate into a high HOMO level. The third organic compound layer, because of its function, can also be called a hole blocking layer. The third organic compound layer 3 may be formed of multiple layers or a bulk heterojunction layer (mixed layer). Other functional layers may be disposed between the anode and the hole blocking layer.

(8) Protective Layer

The protective layer 7 is formed on the upper portion of the electrode and is preferably an insulating layer. The protective layer may be formed of a single material or a plurality of materials. When formed of a plurality of materials, the protective layer may be a stack of the plurality of layers or a layer in which the plurality of materials are mixed together. Examples of constituent materials of the protective layer include organic materials such as resins, and inorganic materials such as silicon nitride, silicon oxide, and aluminum oxide. The protective layer can be formed by sputtering, atomic layer deposition (ALD), or other methods. Silicon nitride is also expressed as SiNx, and silicon oxide as SiOx. X is a numerical value representing an elemental ratio.

A planarizing layer may be disposed on the protective layer 7. The planarizing layer is disposed in order to eliminate the effect of the surface state of the protective layer on the wavelength selection unit. The planarizing layer can be formed by a known production method such as a coating method or a vacuum deposition method. For example, chemical-mechanical polishing (CMP) may optionally be performed.

Examples of materials of the planarizing layer include organic materials such as resins, and inorganic materials such as SiNx, SiOx, and $Al_2O_3$. The planarizing layer may be made of an organic compound or a mixture thereof. The planarizing layer can be formed by the same method as that for the protective layer.

(9) Wavelength Selection Unit

The wavelength selection unit 8 is disposed on the planarizing layer. In the case where the planarizing layer is not provided, the wavelength selection unit is disposed on the protective layer. In other words, the wavelength selection unit is disposed on the light incident side of the photoelectric conversion element. Examples of the wavelength selection unit include color filters, scintillators, and prisms.

Color filters transmit light having a predetermined wavelength more than light having other wavelengths. For example, by using three types of filters, that is, RGB filters, the entire visible light range can be covered. When the three RGB filters are used, the color filters may be arranged in the Bayer pattern, the delta pattern, or other patterns. The wavelength selection unit may be a prism that separates only light having a predetermined wavelength.

The position of the wavelength selection unit 8 is not limited to the position shown in FIG. 3. The wavelength selection unit is disposed at any position in a light path extending from a subject or a light source to the photoelectric conversion layer 1.

(10) Lens

The microlens 9 is an optical member for collecting external light into the photoelectric conversion layer. Although FIG. 3 illustrates a hemispheric lens, the microlens may have any other shape.

The microlens is made of, for example, quartz, silicone, or an organic resin. The shape and the material of the microlens are not limited as long as the collection of light is not impaired.

(11) Other Configurations

The photoelectric conversion element may include another photoelectric conversion element on the electrode. The use of the other photoelectric conversion element that photoelectrically converts light having a different wavelength enables light beams having different wavelengths to be detected at the same or substantially the same in-plane position on the substrate.

The photoelectric conversion element may further include another organic compound layer that photoelectrically converts light having a wavelength different from the wavelength of light photoelectrically converted by the organic compound layer. The organic compound layer and the other organic compound layer may be stacked on top of each other. This configuration, as with the configuration in which photoelectric conversion elements are stacked on top of each other, enables light beams having different wavelengths to be detected at the same position or substantially the same position on the substrate. Image pickup element according to embodiment and image pickup apparatus including the same (1) Image Pickup Element The photoelectric conversion element according to the present embodiment can be used for an image pickup element. The image pickup element includes a plurality of photoelectric conversion elements serving as light-receiving pixels, a readout circuit connected to the photoelectric conversion elements, and a signal processing circuit connected to the readout circuit. Information based on charges that have been read out is transmitted to a signal processing unit connected to the image pickup element. The signal processing unit may be, for example, a CMOS sensor or a CCD sensor. Information acquired by the light-receiving pixels is gathered and transmitted to the signal processing unit, whereby an image is formed.

The image pickup element includes the plurality of photoelectric conversion elements, and the plurality of photoelectric conversion elements may include different color filters. The different color filters transmit light beams having different wavelengths. Specifically, the plurality of photoelectric conversion elements may include RGB color filters.

The plurality of photoelectric conversion elements may include the photoelectric conversion layer as a common layer. The term "common layer" means that the photoelectric conversion layer of one photoelectric conversion element and the photoelectric conversion layer of a photoelectric conversion element adjacent thereto are joined together.

Figure 4:
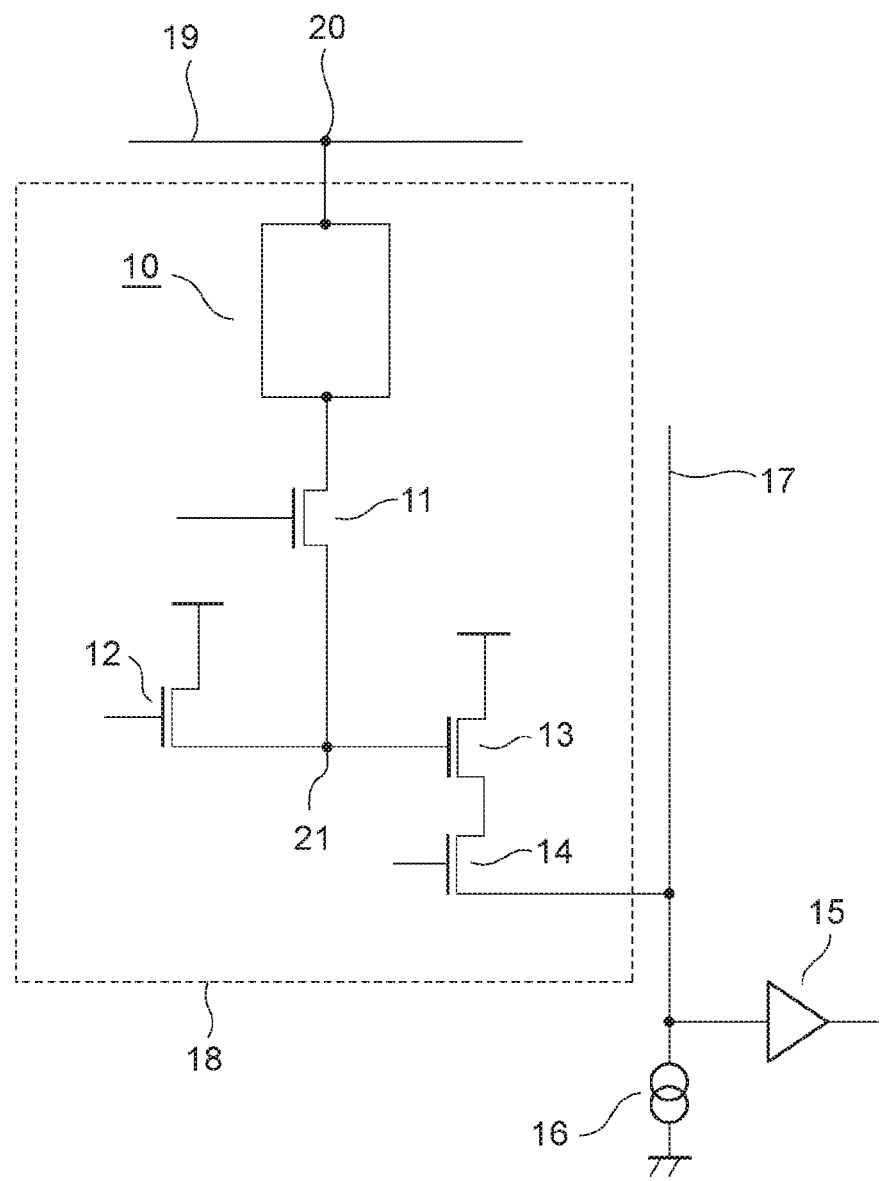
FIG. 4 is a schematic diagram illustrating an example of a pixel circuit including an organic photoelectric conversion element according to an embodiment.

FIG. 4 is a circuit diagram of a pixel including the photoelectric conversion element according to the present embodiment. A photoelectric conversion element 10 is connected to a common line 19 at a node A 20. The common line may be connected to the ground.

A pixel 18 may include the photoelectric conversion element 10 and a readout circuit for reading a signal generated in a photoelectric conversion unit. The readout circuit may include, for example, a transfer transistor 11 electrically connected to the photoelectric conversion element, an amplifier transistor 13 including a gate electrode electrically connected to the photoelectric conversion element 10, a selection transistor 14 that selects a pixel from which information is read out, and a reset transistor 12 that supplies a reset voltage to the photoelectric conversion element.

The transfer by the transfer transistor 11 may be controlled with a gate voltage. The supply of a reset voltage by the reset transistor may be controlled with a voltage applied to the gate. The selected or unselected state of the selection transistor is determined by the gate voltage.

The transfer transistor 11, the reset transistor 12, and the amplifier transistor 13 are connected together at a node B 21. The transfer transistor may be omitted in some configurations.

The reset transistor 12 supplies a voltage to reset the potential at the node B. The supply of the voltage can be controlled by applying a signal to the gate of the reset transistor. The reset transistor may be omitted in some configurations.

The amplifier transistor 13 generates a current depending on the potential at the node B. The amplifier transistor is connected to the selection transistor 14 that selects a pixel from which a signal is output. The selection transistor 14 is connected to a current source 16 and a column output unit 15. The column output unit 15 is connected to a signal processing unit.

The selection transistor 14 is connected to a vertical output signal line 17. The vertical output signal line 17 is connected to the current source 16 and the column output unit 15.

Figure 5:
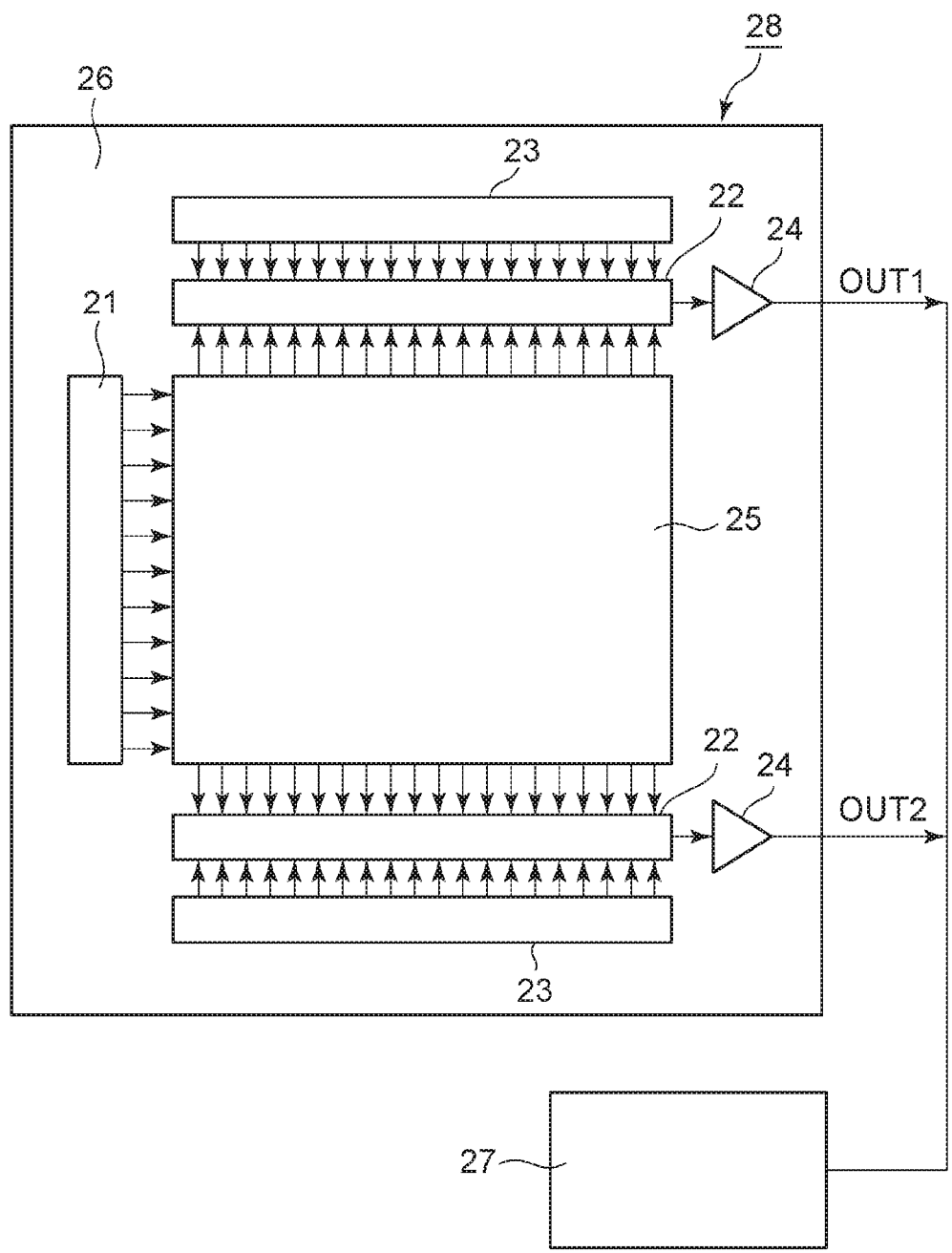
FIG. 5 is a schematic diagram illustrating an example of a peripheral circuit including an organic photoelectric conversion element according to an embodiment.

FIG. 5 schematically illustrates an image pickup element according to an embodiment. An image pickup element 28 includes an image pickup region 25 and a peripheral region 26. The image pickup region 25 includes a two-dimensional array of pixels. The region excluding the image pickup region is the peripheral region. The peripheral region includes a vertical scanning circuit 21, a readout circuit 22, a horizontal scanning circuit 23, and an output amplifier 24. The output amplifier is connected to a signal processing unit 27. The signal processing unit performs signal processing on the basis of information read by the readout circuit. The signal processing unit may be, for example, a CCD circuit or a CMOS circuit.

The readout circuit 22 includes, for example, a column amplifier, a correlated double sampling (CDS) circuit, and an adding circuit. The readout circuit 22 performs amplification or addition of signals read, via a vertical signal line, from pixels in a row selected by the vertical scanning circuit 21. The column amplifier, the CDS circuit, the adding circuit, and so forth are disposed, for example, for each pixel column or for every two or more pixel columns. The CDS circuit performs CDS signal processing and kTC noise reduction. The horizontal scanning circuit 23 produces a signal for sequentially reading a signal from the readout circuit 22. The output amplifier 24 amplifies a signal from a column selected by the horizontal scanning circuit 23 and outputs the signal.

The above configuration is only an example of a photoelectric conversion apparatus, and the present embodiment is not limited to this configuration. The readout circuit 22, the horizontal scanning circuit 23, and the output amplifier 24 are each disposed above and below the image pickup region 25 to constitute two output paths. The number of output paths may be three or more. Signals from the output amplifiers are synthesized into an image signal in the signal processing unit.

(2) Image Pickup Apparatus

The image pickup element according to the present embodiment can be used for an image pickup apparatus. The image pickup apparatus includes an image pickup optical system including a plurality of lenses and an image pickup element that receives light that has passed through the image pickup optical system. The image pickup apparatus includes the image pickup element and a housing that houses the image pickup element. The housing may have a joint connectable to the image pickup optical system. More specifically, the image pickup apparatus is a digital camera or a digital still camera.

The image pickup apparatus may further include a communication unit that allows a captured image to be viewed from the outside. The communication unit may include a receiving unit that receives a signal from the outside and a transmitting unit that transmits information to the outside. Signals received by the receiving unit control at least one of an image pickup range, a start of image pickup, and an end of image pickup of the image pickup apparatus. The transmitting unit may transmit not only captured images but also information such as warning about images, remaining data capacity, and remaining power.

When including a receiving unit and a transmitting unit, the image pickup apparatus can be used as a network camera.

EXAMPLES

Example 1: Synthesis of Exemplary Compound A1

Exemplary compound A1 was synthesized according to the following synthesis scheme.

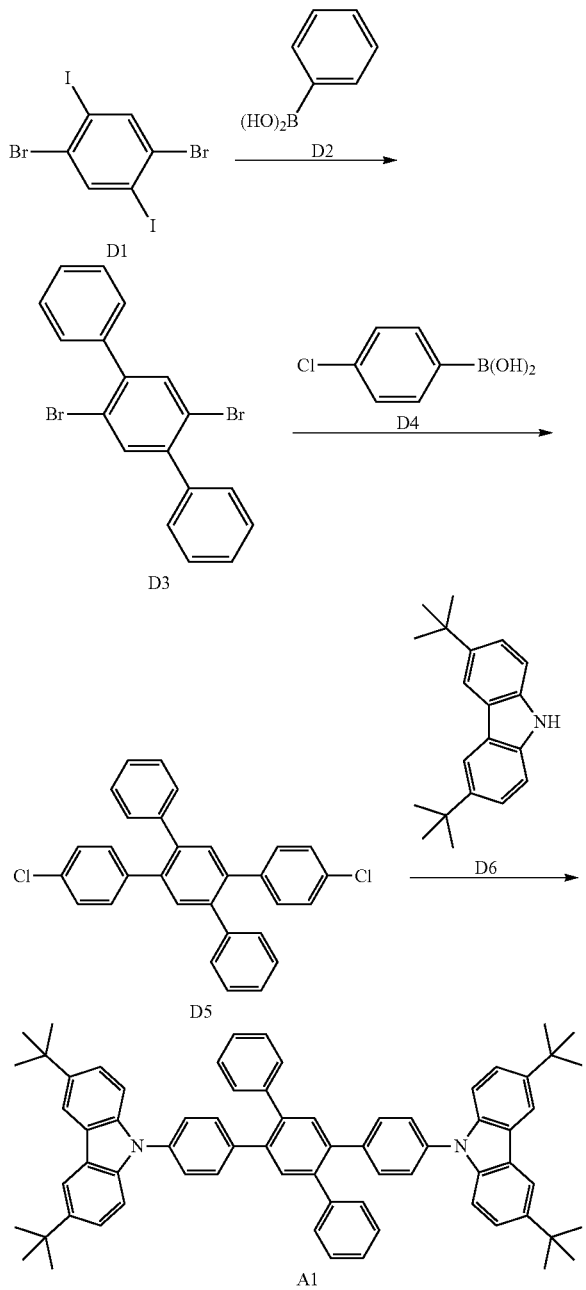

(1) Synthesis of Compound D3

The following reagents and solvents were placed in a 300 mL recovery flask.

Compound D1: 2.00 g (4.10 mmol)
Compound D2: 1.83 g (10.3 mmol)
Tetrakis(triphenylphosphine)palladium(0): 95 mg (0.08 mmol)
Toluene: 40 ml
Ethanol: 20 ml
2M aqueous cesium carbonate solution: 40 ml Next, the reaction solution was heated to reflux with stirring for 7 hours in a nitrogen atmosphere. After completion of the reaction, the reaction product was extracted with chloroform. The organic layer obtained by the extraction was dried over sodium sulfate and then concentrated under reduced pressure to obtain a crude product. Next, the crude product was purified by silica gel column chromatography (eluent: chloroform/heptane=1/10) to obtain 1.55 g of compound D3 (yield: 75%).

(2) Synthesis of Compound D5

The following reagents and solvents were placed in a 300 mL three-necked flask.

Compound D3: 1.50 g (3.00 mmol)
Compound D4: 2.49 g (15.9 mmol)
Tetrakis(triphenylphosphine)palladium(0): 92 mg (0.08 mmol)
Toluene: 40 ml
Ethanol: 20 ml
2M aqueous cesium carbonate solution: 40 ml Next, the reaction solution was heated to reflux with stirring for 7 hours in a nitrogen atmosphere. After completion of the reaction, the reaction product was extracted with chloroform. The organic layer obtained by the extraction was dried over sodium sulfate and then concentrated under reduced pressure to obtain a crude product. Next, the crude product was purified by silica gel column chromatography (eluent: chloroform/heptane=1/10) to obtain 1.25 g of compound D4 (yield: 74%).

(3) Synthesis of Compound A1

The following reagents and solvents were placed in a 300 mL three-necked flask.

Compound D4: 1.20 g (2.13 mmol)
Compound D5: 2.75 g (9.85 mmol)
Tris(dibenzylideneacetone)dipalladium(0): 150 mg (0.16 mmol)
Xphos: 234 mg (0.49 mmol)
Dehydrated xylene: 90 ml
Sodium t-butoxide: 945 mg (9.85 mmol)

Next, the reaction solution was heated to reflux with stirring for 7 hours in a nitrogen atmosphere. After completion of the reaction, the reaction product was filtered through a membrane filter to obtain a filtrate. The filtrate obtained was washed with water, dried over sodium sulfate, and then concentrated under reduced pressure to obtain a crude product. Next, the crude product was purified by silica gel column chromatography (eluent: toluene) and washed by heating dispersion with ethanol to obtain 0.6 g of compound A1 (yield: 27%).

Exemplary compound A1 was identified by the following method.

Matrix-assisted laser desorption/ionization time-of-flight mass spectrometry (MALDI-TOF-MS) (Autoflex LRF manufactured by Bruker)

Measured value: m/z=937.47, calculated value: $C_{70}H_{68}N_2$=937.30

Measurement of Thermophysical Properties

The glass transition temperature of exemplary compound A1 was measured by DSC to be 180° C.

Example 2: Synthesis of Exemplary Compound A2

Exemplary compound A2 was synthesized in the same manner as in Example 1 except that compound D2 was replaced with compound D7 in the step (1).

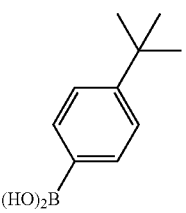

D7

The compound obtained was identified and measured for its thermophysical properties. The results are shown below.

MALDI-TOF-MS

Measured value: m/z=1049.84, calculated value: $C_{70}H_{68}N_2$=1049.51

Measurement of Glass Transition Temperature

Glass transition temperature: 200° C.

Example 3: Synthesis of Exemplary Compound A15

Exemplary compound A15 was synthesized in the same manner as in Example 1 except that compound D2 was replaced with compound 7 in the step (1) and that compound D4 was replaced with compound D8 in the step (2).

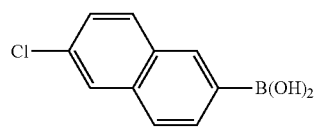

D8

The compound obtained was identified and measured for its thermophysical properties. The results are shown below.

MALDI-TOF-MS

Measured value: m/z=1149.56, calculated value: $C_{86}H_{68}NO_2$=1149.63

Measurement of Glass Transition Temperature

Glass transition temperature: 230° C.

Example 4: Synthesis of Exemplary Compound A9

Exemplary compound A9 was synthesized according to the following synthesis scheme.

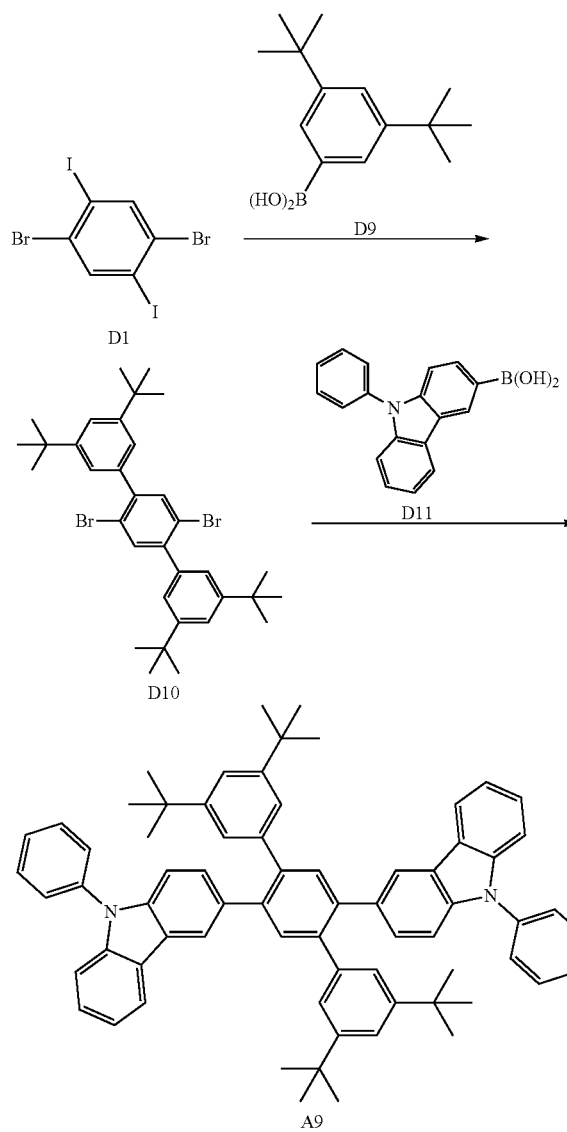

(1) Synthesis of Compound D10

The following reagents and solvents were placed in a 300 mL recovery flask.
Compound D1: 2.00 g (4.10 mmol)
Compound D9: 1.83 g (10.3 mmol)
Tetrakis(triphenylphosphine)palladium(0): 95 mg (0.08 mmol)
Toluene: 40 ml
Ethanol: 20 ml
2M aqueous cesium carbonate solution: 40 ml Next, the reaction solution was heated to reflux with stirring for 7 hours in a nitrogen atmosphere. After completion of the reaction, the reaction product was extracted with chloroform. The organic layer obtained by the extraction was dried over sodium sulfate and then concentrated under reduced pressure to obtain a crude product. Next, the crude product was purified by silica gel column chromatography (eluent: chloroform/heptane=1/10) to obtain 1.55 g of compound D3 (yield: 75%).

(2) Synthesis of Compound A9

The following reagents and solvents were placed in a 300 mL three-necked flask.
Compound D10: 1.50 g (3.00 mmol)
Compound D11: 2.49 g (15.9 mmol)
Tetrakis(triphenylphosphine)palladium(0): 92 mg (0.08 mmol)
Toluene: 40 ml
Ethanol: 20 ml
2M aqueous cesium carbonate solution: 40 ml Next, the reaction solution was heated to reflux with stirring for 7 hours in a nitrogen atmosphere. After completion of the reaction, the reaction product was extracted with chloroform. The organic layer obtained by the extraction was dried over sodium sulfate and then concentrated under reduced pressure to obtain a crude product. Next, the crude product was purified by silica gel column chromatography (eluent: chloroform/heptane=1/10) to obtain 1.25 g of compound A9 (yield: 74%).

The compound obtained was identified and measured for its thermophysical properties. The results are shown below.
MALDI-TOF-MS
Measured value: m/z=937.26, calculated value: $C_{70}H_{68}N_2$=937.30
Measurement of Glass Transition Temperature
Glass transition temperature: 190° C.

Example 5: Synthesis of Exemplary Compound A25

Exemplary compound A25 was synthesized in the same manner as in Example 4 except that compound D9 was replaced with compound D12 in the step (1) and that compound D11 was replaced with compound D13 in the step (2).

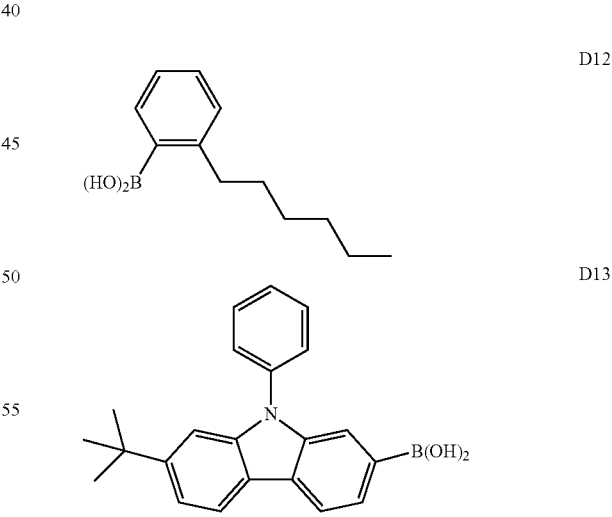

The compound obtained was identified and measured for its thermophysical properties. The results are shown below.
MALDI-TOF-MS
Measured value: m/z=937.28, calculated value: $C_{78}H_{84}N_2$=1049.51
Measurement of Glass Transition Temperature
Glass transition temperature: 190° C.

Example 6: Synthesis of Exemplary Compound B3

Exemplary compound B3 was synthesized in the same manner as in Example 1 except that compound D2 was replaced with compound D7 in the step (1) and that compound D4 was replaced with compound D14 in the step (2).

D14: [3-chlorophenylboronic acid structure: Cl-C6H4-B(OH)2]

The compound obtained was identified and measured for its thermophysical properties. The results are shown below.
MALDI-TOF-MS
Measured value: m/z=1049.73, calculated value: $C_{78}H_{84}N_2$=1049.51
Measurement of Glass Transition Temperature
Glass transition temperature: 190° C.

Example 7: Synthesis of Exemplary Compound C6

Exemplary compound C6 was synthesized in the same manner as in Example 1 except that compound D2 was replaced with compound D15 in the step (1).

D15: [benzothiophene-boronic acid structure: (HO)2B-benzothiophene]

The compound obtained was identified and measured for its thermophysical properties. The results are shown below.
MALDI-TOF-MS
Measured value: m/z=1049.51, calculated value: $C_{74}H_{68}N_2S_2$=1049.48
Measurement of Glass Transition Temperature
Glass transition temperature: 190° C.

Example 8: Synthesis of Exemplary Compound C17

Exemplary compound C17 was synthesized in the same manner as in Example 1 except that compound D2 was replaced with compound D16 in the step (1).

D16: [pyridine-boronic acid structure: (HO)2B-pyridine]

The compound obtained was identified and measured for its thermophysical properties. The results are shown below.
MALDI-TOF-MS
Measured value: m/z=939.21, calculated value: $C_{68}H_{66}N_4$=939.28
Measurement of Glass Transition Temperature
Glass transition temperature: 190° C.

Comparative Example 1: Synthesis of Comparative Compound 2

Comparative compound 2 was synthesized in the same manner as in Example 1 except that compound D6 was replaced with compound D17 in the step (3).

D17: [carbazole structure]

The compound obtained was identified and measured for its thermophysical properties. The results are shown below.
MALDI-TOF-MS
Measured value: m/z=712.41, calculated value: $C_{54}H_{66}N_2$=712.88
Measurement of Glass Transition Temperature
Glass transition temperature: 160° C.

Comparative Example 2: Synthesis of Comparative Compound 3

Comparative compound 3 was synthesized in the same manner as in Example 1 except that compound D2 was replaced with compound D7 in the step (1) and that compound D6 was replaced with compound D18 in the step (3).

D18: [3,6-diphenylcarbazole structure]

The compound obtained was identified. The results are shown below.
MALDI-TOF-MS
Measured value: m/z=1017.56, calculated value: $C_{78}H_{52}N_2$=1017.26
Sublimation purification of comparative compound 3 was resulted in failure, and thus an element containing comparative compound 3 could not be fabricated.

Example 9: Fabrication of Photoelectric Conversion Element

An organic photoelectric conversion element was fabricated in a manner described below. In the organic photoelectric conversion element, a cathode, an electron blocking layer (a first organic compound layer), a photoelectric conversion layer (a second organic compound layer), a hole blocking layer (a third organic compound layer), and an anode were sequentially formed on a substrate.

First, an indium zinc oxide film was formed on a Si substrate and then patterned into a desired shape, thereby forming a cathode. The thickness of the cathode was set to 100 nm. The substrate having the cathode formed thereon was used as a substrate provided with an electrode in the following process.

Next, organic compound layers and an electrode shown in Table 2 below were successively formed on the substrate provided with an electrode. The photoelectric conversion layer was formed by co-deposition, and its mixing ratio and thickness are as shown in the table. At this time, the electrode area of the counter electrode (anode) was set to 3 mm$^2$. Thereafter, a sealing layer was formed using SiN.

TABLE 2

| | Constituent material | Thickness (nm) |
|---|---|---|
| Electron blocking layer | Exemplary compound A2 | 100 |
| Photoelectric conversion layer | CG6:CG25 = 50:50 (weight ratio) | 400 |
| Hole blocking layer | Fullerene C60 | 50 |
| Electron collecting electrode | Indium zinc oxide | 30 |

Examples 10 to 19 and Comparative Examples 3 to 5: Fabrication of Photoelectric Conversion Element Organic photoelectric conversion elements were fabricated in the same manner as in Example 1 except that the electron blocking layer, the photoelectric conversion layer, and the hole blocking layer were appropriately changed as shown in Table 3 below. In Comparative Example 3, comparative compound 3, which was unpurified by sublimation, was used to deposit an electron blocking layer, but the rate of deposition was unstable.

TABLE 3

| | Electron blocking layer | Photoelectric conversion layer | Hole blocking layer |
|---|---|---|---|
| Example 10 | Exemplary compound A2 | CG5:CG25 = 50:50 (weight ratio) | Fullerene 060 |
| Example 11 | Exemplary compound A4 | CG1:CG25:Exemplary compound A2 = 40:40:20 (weight ratio) | HBM1 |
| Example 12 | Exemplary compound A6 | CG2:Fullerene C60 = 20:80 (weight ratio) | HBM1 |
| Example 13 | Exemplary compound A1 | CG2:Fullerene C60 = 30:70 (weight ratio) | HBM2 |
| Example 14 | Exemplary compound A12 | CG18:CG21 = 50:50 (weight ratio) | HBM4 |
| Example 15 | Exemplary compound B1 | CG9:Fullerene C60 = 50:50 (weight ratio) | [60]PCBM |
| Example 16 | Exemplary compound B5 | CG10:Fullerene C60 = 20:80 (weight ratio) | Fullerene C60 |
| Example 17 | Exemplary compound C6 | CG28:Fullerene C60 = 30:70 (weight ratio) | Exemplary compound A2: Fullerene C60 = 30:70 (weight ratio) |
| Example 18 | Exemplary compound A2 | CG30:Fullerene C60 = 50:50 (weight ratio) | Exemplary compound A2: Fullerene C60 = 30:70 (weight ratio) |
| Example 19 | Exemplary compound A21 | CG10:CG27 = 50:50 (weight ratio) | Exemplary compoundA21: Fullerene C60 = 30:70 (weight ratio) |
| Comparative Example 3 | Comparative compound 2 | CG6:CG25 = 50:50 (weight ratio) | Fullerene C60 |
| Comparative Example 4 | none | CG1:CG25 = 50:50 (weight ratio) | Comparative compound 2: Fullerene C60 = 30:70 (weight ratio) |
| Comparative Example 5 | Comparative compound 3 | CG6:CG25 = 50:50 (weight ratio) | Fullerene C60 |

Evaluation of Properties of Photoelectric Conversion Elements

The photoelectric conversion elements obtained in Examples and Comparative Examples were measured and evaluated for their properties.

(1) Current Properties

Specifically, a voltage of 5 V was applied to each element, and the current flowing through the element at this time was measured. For each of the organic photoelectric conversion elements fabricated in Examples, the ratio of a current in a bright place to a current in a dark place (current in bright place)/(current in dark place) was 100 or more. This indicates that the organic photoelectric conversion elements fabricated in Examples function well.

(2) Evaluations of Quantum Yield (External Quantum Yield) and Dark Current

The organic photoelectric conversion elements obtained were evaluated for changes in dark current and external quantum efficiency before and after annealing. The effect of annealing in reducing dark current was evaluated according to the following criteria: when the dark current after annealing was less than 0.5 relative to the dark current before annealing taken as 1, the element was graded as A; when it was 0.5 or more and less than 1, the element was graded as B; and when it was 1.0 or more, the element was graded as C.

The stability of element properties after annealing was evaluated according to the following criteria: when the external quantum efficiency after annealing was 1.0 or more relative to the external quantum efficiency before annealing taken as 1, the element was graded as A; when it was 0.8 or more and less than 1.0, the element was graded as B; and when it was less than 0.8, the element was graded as C. The annealing was performed by allowing the element to sit on a hot plate at 170° C. for 30 minutes in the ambient atmosphere.

The dark current was determined as the density of current flowing when the photoelectric conversion element was allowed to sit in a dark place with a voltage of 5 V being applied between the cathode and the anode.

The external quantum efficiency was determined by measuring the density of photocurrent flowing when the photoelectric conversion element was irradiated with monochromatic light with an intensity of 50 μW/cm$^2$ at a maximum absorption wavelength of the element, with a voltage of 5 V being applied between the cathode and the anode of the element.

The photocurrent density was determined by subtracting the dark current density in the dark from the current density at the time of light irradiation. The monochromatic light used for the measurement was obtained by monochromatizing white light emitted from a xenon lamp (Model XB-50101AA-A, manufactured by Ushio, Inc.) with a monochromator (Model MC-10N, manufactured by Ritu Oyo Kougaku Co., Ltd.). The application of voltage to the elements and the measurement of current were performed with a source meter (Model R6243, manufactured by Advantest Corporation). The measurement of the external quantum efficiency was performed from the upper electrode side with light being perpendicularly incident on the element. The results are shown in Table 4.

TABLE 4

|  | Dark current | External quantum efficiency |
|---|---|---|
| Example 9 | A | A |
| Example 10 | A | B |
| Example 11 | A | A |
| Example 12 | B | B |
| Example 13 | B | B |
| Example 14 | A | A |
| Example 15 | A | B |
| Example 16 | A | A |
| Example 17 | B | B |
| Example 18 | A | A |
| Example 19 | B | B |
| Comparative Example 3 | C | B |
| Comparative Example 4 | C | C |
| Comparative Example 5 | C | B |

Table 4 shows that the organic photoelectric conversion elements according to the present invention exhibited significant reductions in dark current after annealing and, in addition, maintained their external quantum efficiency. In particular, when the number of tert-butyl groups was 6 or more, the dark current was greatly reduced after annealing, and good element properties were exhibited. This is probably because an amorphous thin film having high thermal stability was formed. By contrast, the organic photoelectric conversion elements of Comparative Examples exhibited increases in dark current after annealing. This can be explained as follows: when the material forming the electron blocking layer had a low glass transition temperature, crystallization due to annealing resulted in degraded film quality, and when the deposited film had low purity, an impurity level was formed, thus resulting in degradation of element properties.

As described in EXAMPLES above, it was found that the presence of the organic compound according to the present invention in an electron blocking layer can provide an organic photoelectric conversion element with reduced dark current and improved thermal stability.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:
1. An organic compound represented by general formula [1]:

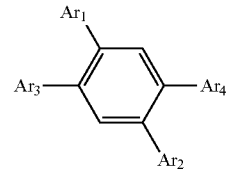

[1]

wherein $Ar_1$ and $Ar_2$ may be the same or different and represent an aromatic hydrocarbon group having 6 to 18 carbon atoms or a heteroaromatic group having 3 to 17 carbon atoms, $Ar_3$ and $Ar_4$ may be the same or different and are selected from the group consisting of substituents represented by general formulae [2a] to [2c], in which * indicates a bonding position to a phenyl group represented by the general formula [1]:

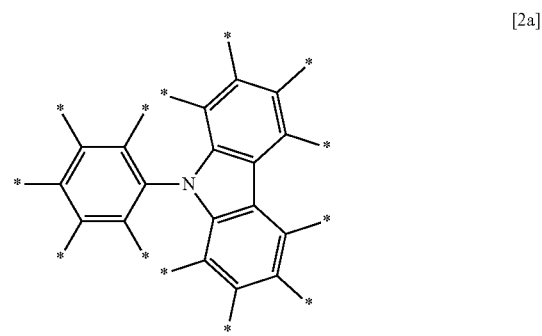

[2a]

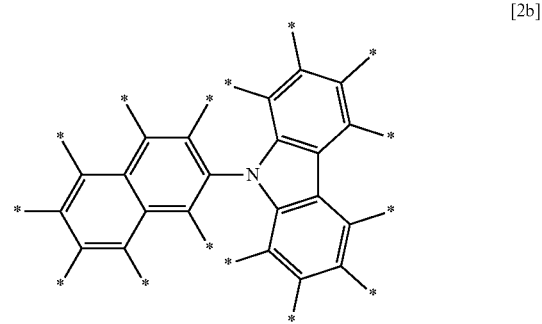

[2b]

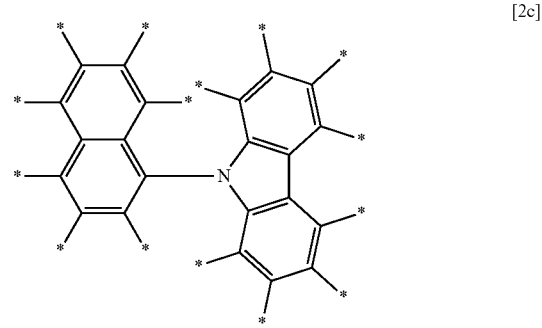

[2c]

$Ar_1$ to $Ar_4$ are each optionally substituted with a substituent selected from the group consisting of a halogen atom, a cyano group, an alkyl group having 1 to 8 carbon atoms, and an alkoxy group having 1 to 8 carbon atoms, the alkyl group being optionally substituted with a fluorine atom, provided that at least one of $Ar_1$ to $Ar_4$ has a tert-butyl group, and a total number of tert-butyl groups in one molecule of the organic compound is 2 or more.

2. The organic compound according to claim 1, wherein $Ar_1$ and $Ar_2$ are each a phenyl group, a naphthyl group, a pyridyl group, a benzothienyl group, or a benzofuranyl group.

3. The organic compound according to claim 1, wherein $Ar_1$ and $Ar_1$ are each the substituent represented by formula [2a].

4. The organic compound according to claim 1, wherein the total number of tert-butyl groups in one molecule of the organic compound is 4 or more.

5. The organic compound according to claim 1, wherein the total number of tert-butyl groups in one molecule of the organic compound is 6 or more.

* * * * *